(12) United States Patent  
Osorio

(10) Patent No.: US 9,204,838 B2  
(45) Date of Patent: Dec. 8, 2015

(54) DETECTING, ASSESSING AND MANAGING EPILEPSY USING A MULTI-VARIATE, METRIC-BASED CLASSIFICATION ANALYSIS

(71) Applicant: Flint Hills Scientific, L.L.C., Lawrence, KS (US)

(72) Inventor: Ivan Osorio, Leawood, KS (US)

(73) Assignee: Flint Hills Scientific, LLC, Lawrence, KS (US)

( * ) Notice: Subject to any disclaimer, the term of this patent is extended or adjusted under 35 U.S.C. 154(b) by 0 days.

(21) Appl. No.: 14/583,187

(22) Filed: Dec. 25, 2014

(65) Prior Publication Data

US 2015/0196246 A1 Jul. 16, 2015

Related U.S. Application Data

(63) Continuation of application No. 14/188,485, filed on Feb. 24, 2014, now Pat. No. 8,945,006, which is a (Continued)

(51) Int. Cl.
| | |
|---|---|
| *A61B 5/00* | (2006.01) |
| *A61B 5/042* | (2006.01) |
| *A61B 5/11* | (2006.01) |
| *A61B 5/145* | (2006.01) |
| *A61N 1/36* | (2006.01) |
| *A61B 5/0205* | (2006.01) |

(Continued)

(52) U.S. Cl.
CPC .............. *A61B 5/4094* (2013.01); *A61B 5/0205* (2013.01); *A61B 5/02055* (2013.01); *A61B 5/042* (2013.01); *A61B 5/0476* (2013.01); *A61B 5/11* (2013.01); *A61B 5/1117* (2013.01); *A61B 5/1118* (2013.01); *A61B 5/14503* (2013.01); *A61B 5/14542* (2013.01); *A61B 5/486* (2013.01); *A61B 5/4836* (2013.01); *A61B 5/4848* (2013.01); *A61B 5/686* (2013.01); *A61B 5/7246* (2013.01); *A61B 5/7264* (2013.01); *A61B 5/7267* (2013.01); *A61B 5/7275* (2013.01); *A61B 5/7282* (2013.01); *A61B 5/742* (2013.01); *A61B 5/743* (2013.01); *A61M 16/1005* (2013.01); *A61N 1/36064* (2013.01); *A61N 1/36135* (2013.01); *A61B 5/02405* (2013.01); *A61B 5/08* (2013.01); *A61B 2560/0475* (2013.01); *A61M 2202/0208* (2013.01); *A61M 2205/3303* (2013.01)

(58) Field of Classification Search
None
See application file for complete search history.

(56) References Cited

U.S. PATENT DOCUMENTS 8,562,524 B2 * 10/2013 Osorio .......................... 600/300  
8,821,418 B2 *  9/2014 Meger et al. .................. 600/595  
(Continued)

*Primary Examiner* — Brian T Gedeon

(57) ABSTRACT

A method for identifying changes in an epilepsy patient's disease state, comprising: receiving at least one body data stream; determining at least one body index from the at least one body data stream; detecting a plurality of seizure events from the at least one body index; determining at least one seizure metric value for each seizure event; performing a first classification analysis of the plurality of seizure events from the at least one seizure metric value; detecting at least one additional seizure event from the at least one determined index; determining at least one seizure metric value for each additional seizure event, performing a second classification analysis of the plurality of seizure events and the at least one additional seizure event based upon the at least one seizure metric value; comparing the results of the first classification analysis and the second classification analysis; and performing a further action.

25 Claims, 17 Drawing Sheets

Related U.S. Application Data continuation of application No. 13/472,365, filed on May 15, 2012, now Pat. No. 8,684,921, which is a continuation-in-part of application No. 13/091,033, filed on Apr. 20, 2011, now Pat. No. 8,562,524, and a continuation-in-part of application No. 13/333,235, filed on Dec. 21, 2011, and a continuation-in-part of application No. 13/040,996, filed on Mar. 4, 2011, now Pat. No. 8,562,523, and a continuation-in-part of application No. 13/288,886, filed on Nov. 3, 2011, which is a continuation-in-part of application No. 13/098,262, filed on Apr. 29, 2011, now Pat. No. 8,382,667, which is a continuation-in-part of application No. 12/896,525, filed on Oct. 1, 2010, now Pat. No. 8,337,404, said application No. 13/091,033 is a continuation-in-part of application No. 13/040,996, filed on Mar. 4, 2011, now Pat. No. 8,562,523.

(51) Int. Cl.
*A61B 5/0476* (2006.01)
*A61M 16/10* (2006.01)
*A61B 5/024* (2006.01)
*A61B 5/08* (2006.01)

(56) References Cited

U.S. PATENT DOCUMENTS

| | | | | |
|---|---|---|---|---|
| 8,909,330 | B2* | 12/2014 | McCombie et al. | 600/513 |
| 8,945,006 | B2* | 2/2015 | Osorio | 600/300 |
| 8,956,294 | B2* | 2/2015 | McCombie et al. | 600/301 |
| 2004/0133119 | A1* | 7/2004 | Osorio et al. | 600/544 |
| 2008/0275349 | A1* | 11/2008 | Halperin et al. | 600/484 |
| 2008/0319281 | A1* | 12/2008 | Aarts | 600/301 |

* cited by examiner

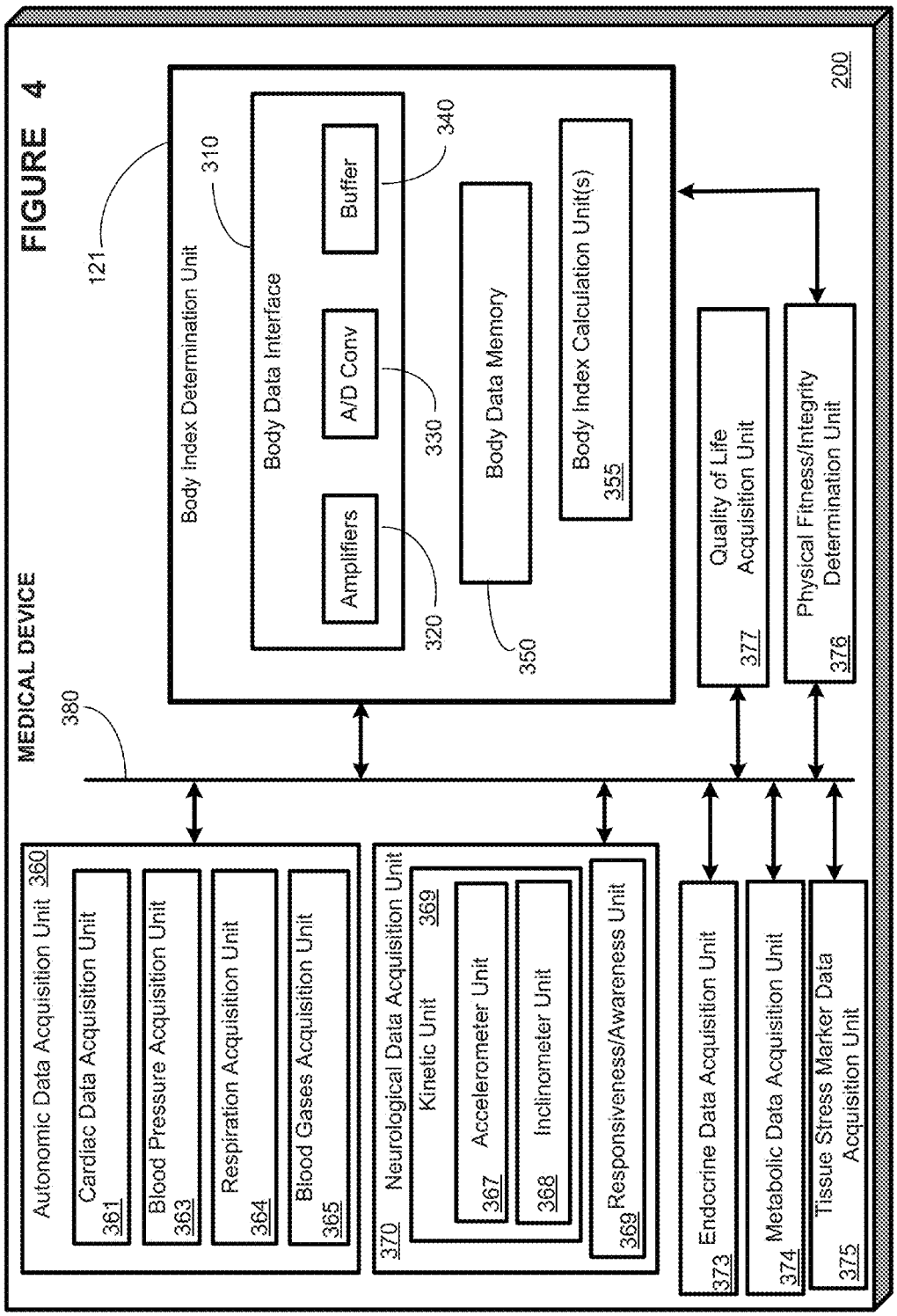

DETECTING, ASSESSING AND MANAGING EPILEPSY USING A MULTI-VARIATE, METRIC-BASED CLASSIFICATION ANALYSIS

CROSS-REFERENCE TO RELATED APPLICATIONS

The present application is a Continuation-in-Part of U.S. patent application Ser. No. 13/091,033, filed Apr. 20, 2011, and Ser. No. 13/333,235, filed Dec. 21, 2011, both pending and both Continuations-in-Part of U.S. patent application Ser. No. 13/040,996, filed Mar. 4, 2011, now pending. The present application is also a Continuation-in-Part of U.S. patent application Ser. No. 13/288,886, filed Nov. 3, 2011, which is a Continuation-in-Part of U.S. patent application Ser. No. 13/098,262, filed Apr. 29, 2011, which is a Continuation-in-Part of U.S. patent application Ser. No. 12/896,525, filed Oct. 1, 2010. Each of U.S. patent application Ser. Nos. 13/091,033, 13/333,235, 13/040,996, 13/288,886, 13/098,262, and 12/896,525 are hereby incorporated by reference in their entirety.

BACKGROUND

1. Field of the Invention

This invention relates generally to medical device systems and, more particularly, to medical device systems and methods capable of assessing and managing epileptic events related to epilepsy based upon seizure classification.

2. Description of the Related Art

Generalized tonic-clonic status epilepticus, referred to herein as Convulsive Status Epilepticus (CSE), is a neurological emergency with an estimated incidence of about 20 out of 100,000 patients. CSE is also associated with a mortality rate between 3% and 40% depending on etiology, age, status type, and status duration and is considered in this disclosure an extreme event. CSE, in particular, requires immediate, aggressive, and effective treatment to stop seizure activity, to prevent neuronal damage, systemic complications, and the possibility of death. Most investigations on prognosis of status epilepticus (SE) have focused on mortality. Some research suggests that SE outcome basically depends on the etiological and biological background of the SE episode, and that the earlier the therapeutic intervention, the higher the probability of controlling it. Additionally, non-convulsive status epilepticus (nCSE), while not a medical emergency of the magnitude of CSE, is also an extreme epileptic event because it increases the risk of bodily injury and neurologic deficits such as permanent, potentially severe impairment of memory.

SE and CSE are defined based on the duration of a single seizure and its variations, or on the lack of recovery of certain neurologic functions to their inter-ictal (baseline) levels in the context of closely spaced seizures. While it is common to focus on seizure duration or frequency as measured from patient EEG, and whether the patient is conscious/aware or not, such a focus has important limitations, because signals or indices from other body systems (such as cardio-vascular, respiratory, endocrine, and metabolic) are adversely impacted by the seizures, undergoing extreme, life-threatening changes that do not receive the same attention as the seizures. These cardio-respiratory, metabolic, and endocrine extreme changes may directly contribute to the morbidity and mortality associated with SE. In the present state of the art, SE is viewed and treated narrowly (and ineffectively) as mainly a brain condition. Current diagnostic tools do not facilitate early detection/anticipation of extreme epileptic events, which may contribute to serious neurological and medical sequelae or even death associated with SE.

Sudden Unexpected Death in Epilepsy, or "SUDEP," another extreme epileptic event, is a phenomenon in which a patient with epilepsy dies unexpectedly and without an apparent, outstanding cause—that is, the death is unexplained since autopsy results are unrevealing. One of the main risk factors for SUDEP is the lack of seizure control with first line drugs prescribed alone or in any safe combination and dosage. Whether or not the first in a chain of ultimately fatal events leading to SUDEP is a seizure, the defining event is likely to be either cardiac (e.g., ventricular fibrillation or asystole) or respiratory (e.g., apnea) or both. Currently, the monitoring, detection, prediction and prevention of SUDEP are inadequate and markedly limited in breadth and depth of scope, as demonstrated by the fact that such deaths are, by definition, unexpected.

SE and/or CSE alter autonomic nervous system function, and SUDEP may be caused by autonomic dysfunction. Brain/neurological activity, such as electrical activity, whether normal or abnormal, and autonomic functions (e.g., cardiovascular activity, respiration, etc.), referred to herein as body signals, are functionally tightly coupled, and monitoring these body signals may provide valuable information. SE and CSE also increase the risk of body injuries associated with seizures which may result from the impairment of the patient's consciousness or awareness. Injuries such as bone fractures and burns, for example, and adverse changes in body functions during a seizure, may increase the risk of mortality to the patient independent of the seizure itself. Such injuries may qualify a seizure as an extreme event regardless of its severity or closeness in time to a prior seizure (inter-seizure interval). On the other hand, certain seizure severity or inter-seizure interval values may suffice to classify a seizure as an extreme event irrespective of the impact on body functions/systems.

SUMMARY OF EMBODIMENTS

In one embodiment, the present disclosure relates to a method for identifying changes in an epilepsy patient's disease state. The method comprises receiving at least one body data stream; determining at least one of an autonomic index, a neurologic index, a metabolic index, an endocrine index, a tissue index, or a tissue stress index, a physical fitness or body integrity index based upon the at least one body data stream; detecting a plurality of seizure events based upon the at least one determined index; determining at least one seizure metric value for each seizure event in the plurality of seizure events; performing a first classification analysis of the plurality of seizure events based on the at least one seizure metric value for each seizure event; detecting at least one additional seizure event based upon the at least one determined index; determining at least one seizure metric value for each of the at least one additional seizure events, performing a second classification analysis of the plurality of seizure events and the at least one additional seizure event based upon the at least one seizure metric value; comparing the results of the first classification analysis and the second classification analysis; and performing a further action. The further action may be selected from reporting a change from the first classification to the second classification; reporting the absence of a change from the first classification to the second classification; displaying a result of at least one of the first classification analysis, the second classification analysis, and the comparing; identifying the emergence of a new class based on the comparing; identifying the disappearance of a prior class based on the comparing; identifying one or more outlier seizure events not part of any class; identifying an effect of a therapy; providing a therapy to the patient in response to the comparing; identifying a proposed change in therapy; identifying a proposed additional therapy; identifying an extreme seizure event; issuing a warning if a new seizure class appears or an extreme event occurs; and logging to memory the time, date and type of change in the patient's seizures.

In one embodiment, the present disclosure relates to a method comprising identifying at least three initial seizure events in a patient, classifying each initial seizure event into at least a first class, identifying at least one additional seizure event, re-classifying the first class based upon at least one of the initial seizure events and the at least one additional seizure event; and performing a responsive action based upon the re-classifying.

In one embodiment, the present disclosure relates to a method comprising detecting a plurality of seizure events based upon body data of the patient; determining, for each seizure event, at least one seizure metric value characterizing the seizure event, where each of the at least one seizure metric values comprises one of an autonomic index, a neurologic index, a metabolic index, an endocrine index, a tissue index, or a tissue stress index; performing a first classification analysis of a first portion of the plurality of seizure events, the classification analysis comprising assigning each seizure event in the first portion to at least one seizure class based upon the proximity of the seizure metric values to each other; performing a second classification analysis of a second portion of the plurality of seizure events, the classification analysis comprising assigning each seizure event in the second portion to at least one seizure class based upon the proximity of the seizure metric values, wherein said second portion comprises at least one seizure event not present in the first portion; comparing the results of the first classification analysis and the second classification analysis; and performing a further action. The further action may be an action selected from: reporting a change from the first classification to the second classification; reporting the absence of a change from the first classification to the second classification; displaying a result of at least one of the first classification analysis, the second classification analysis, and the comparing; identifying the emergence of a new class based on the comparing; identifying the disappearance of a prior class based on the comparing; identifying one or more outlier seizure events not part of any class; identifying an effect of a therapy; providing a therapy to the patient in response to the comparing; identifying a proposed change in therapy; identifying a proposed additional therapy; identifying an extreme seizure event; identifying a worsening trend in the patient's seizures; identifying an improvement trend in the patient's seizures; downgrading the patient's condition in response to a worsening in the patient's seizures; and upgrading the patient's condition in response to an improvement in the patient's seizures.

In one embodiment, the present disclosure relates to a method comprising detecting a plurality of seizure events in a first time period, wherein each of the seizure events is detected based upon body data of the patient; determining at least one seizure metric value for each seizure event of the plurality of seizure events; performing a first classification analysis of a first portion of the plurality of seizure events, wherein the detection of each seizure in the first portion occurred within a second time period within said first time period, wherein said first classification analysis comprises identifying at least a first seizure class and a second seizure class based on the at least one seizure metric value, wherein the second seizure class comprises seizures that are more severe than seizures in the first seizure class; performing a second classification analysis of a second portion of the plurality of seizure events, wherein the detection of each seizure in the second portion occurred within a third time period, and wherein the third time period is a period within the first time period, and at least a portion of the third time period is not within the second time period, wherein the second classification analysis comprises determining, for each seizure event in the third time period, whether the seizure event is within the first seizure class and within the second seizure class, based on the at least one seizure metric value; identifying at least one of a change in the first seizure class and the second seizure class between the first classification analysis and the second classification analysis; and performing a responsive action based on the identifying.

In one embodiment, the present disclosure relates to a non-transitory computer readable program storage unit encoded with instructions that, when executed by a computer, perform a method as described above and/or herein.

BRIEF DESCRIPTION OF THE DRAWINGS

The invention may be understood by reference to the following description taken in conjunction with the accompanying drawings, in which like reference numerals identify like elements, and in which:

FIG. 4 provides a stylized diagram of a medical device and different data acquisition units that may provide output(s) used by a body index determination unit, in accordance with one illustrative embodiment of the present invention;

Figure 1:
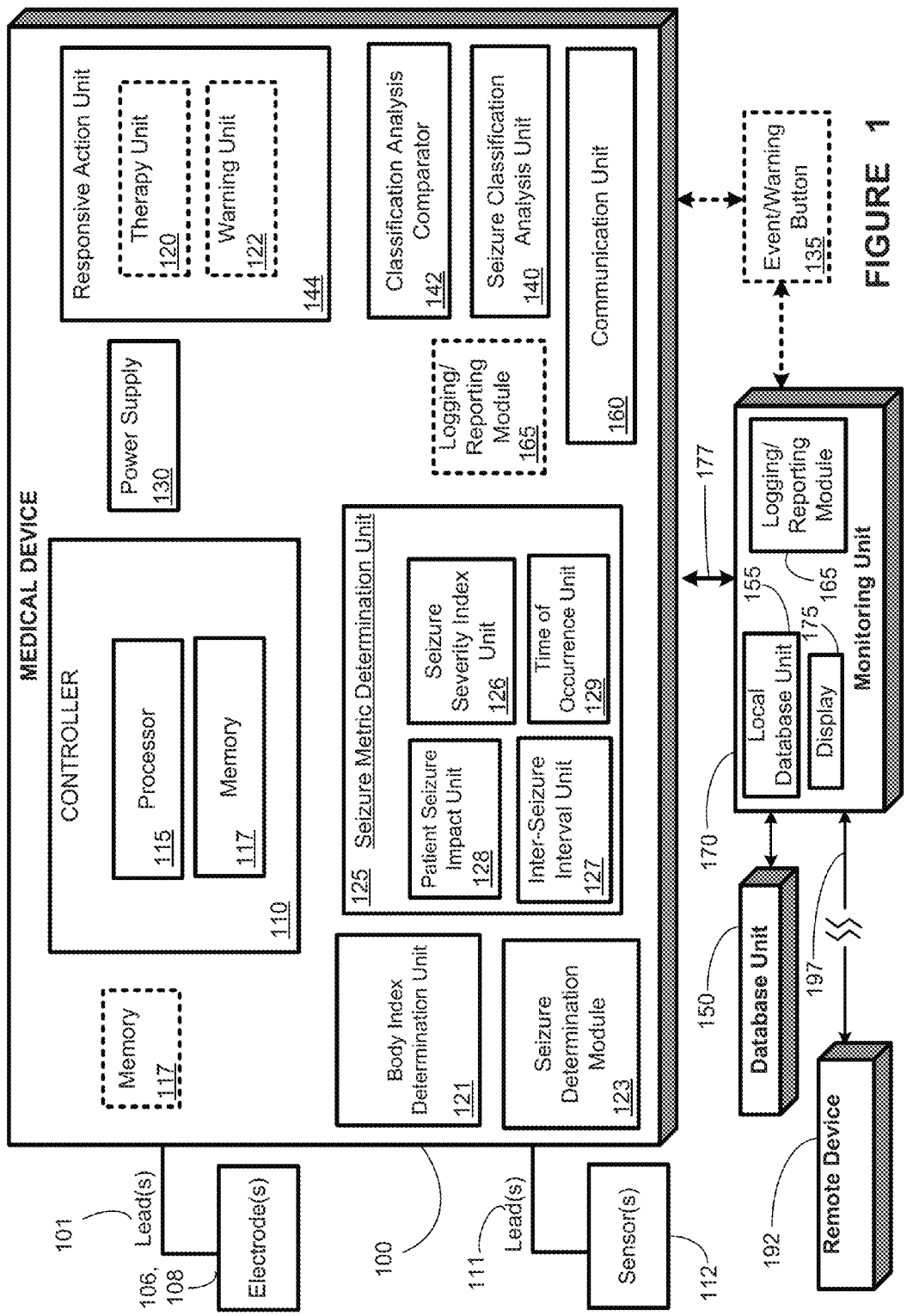
FIG. 1 illustrates a medical device for detecting and classifying seizure events related to epilepsy, and comparing classification analyses of seizure events, according to an illustrative embodiment of the present invention.

The invention is susceptible to various modifications and alternative forms. Specific embodiments have been shown by way of example in the drawings and are herein described in detail, but are not intended to limit the invention to the particular forms disclosed, but on the contrary, the intention is to cover all modifications, equivalents, and alternatives falling within the spirit and scope of the invention as claimed.

DETAILED DESCRIPTION OF SPECIFIC EMBODIMENTS

Illustrative embodiments of the invention are described herein. In the interest of clarity, not all features of an actual implementation are described in this specification. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to. "Couple" or "couples" are intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. "Or" is used in the inclusive sense (i.e., "and/or") unless a specific use to the contrary is explicitly stated. "Adapted to" and "capable of" as used herein may imply, among other things, that a device has a structure sufficient to perform some task or operation, and are not used to state (implicitly or explicitly) mere intended use limitations in the description and claims of the instant application.

The term "electrode" or "electrodes" described herein may refer to one or more stimulation electrodes (i.e., electrodes for delivering a therapeutic signal to a tissue), sensing electrodes (i.e., electrodes for sensing a physiological indication of a patient's body), and/or electrodes that are capable of both delivering a therapeutic signal and sensing body signals.

"Specific care" in the context of epilepsy patients may be patient care that is targeted at a seizure event itself, such as electrical stimulation, seizure drug treatments, and the like. "Supportive care" for epilepsy patients may involve care targeted to supporting or maintaining vital function(s) within their normal ranges (e.g., temperature, breathing, blood oxygenation, heart rate, blood pressure, acid-base balance, and electrolytes, among others, and minimizing the risk of tissue damage through, e.g., body and/or brain cooling, or administration of medications with antioxidant properties and/or the like).

The term "occurrence" used in reference to epileptic events may mean a risk of occurrence, an increased/increasing risk of occurrence, or an actual occurrence of such events. The terms "seizure event" and "epileptic event" may be used interchangeably.

The terms "microscopic," "mesoscopic," and "macroscopic" may refer to time periods for observation or analysis of seizure events and/or extreme seizure events, body changes such as heart wave and heart wave complex morphology, heart rate variability, and/or other body data described herein. "Microscopic" may correspond to the scale of observation of at least part of a heart beat cycle, such as a P-wave, a QRT complex, a T-wave, a PQ interval, an ST segment, etc. Microscopic may also correspond to a period of time that is less than a "mesoscopic" time period (e.g., less than 10 seconds). "Mesoscopic" may correspond to a scale of observation of several seconds to tens of seconds (e.g., 10-300 seconds), which may, for example, capture a change in a patient's heart rate plot representative of a state change. "Macroscopic" may correspond to a scale of observation longer than 300 seconds that may be used to encompass more than the information contained in the "mesoscopic" scale or window as described above. In the context of the description provided herein, the term "window" may be used to refer to one or more of the "mesoscopic," "microscopic," and "macroscopic" time periods described above.

Figure 2:
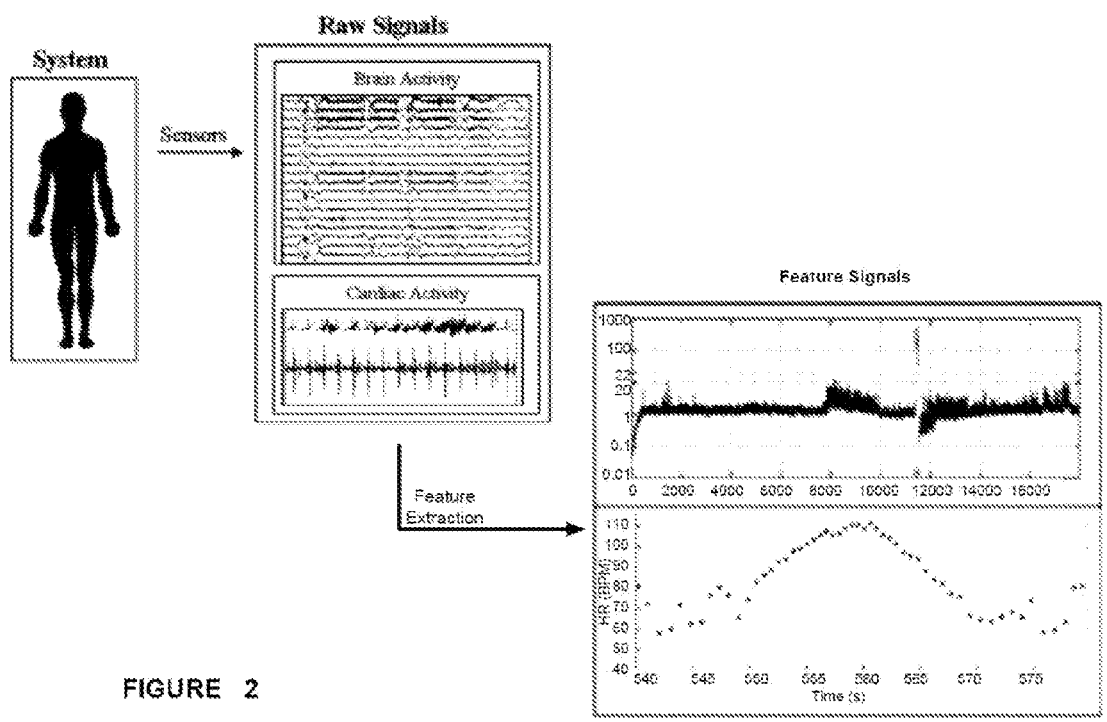
FIG. 2 illustrates a medical device system for detecting and classifying seizure events related to epilepsy from sensed body data processed to extract features indicative of aspects of the patient's epilepsy condition.

Seizure events may be detected based on effects of the seizure upon one or more body systems of the patient. For example, seizures may be identified from brain wave changes as measured by the patient's EEG signal. In some patients, seizure events are accompanied by tachycardia before, at the same time as, or after the electrographic onset of the seizure. Automated systems have been proposed to detected seizure events. As shown in FIG. 2, one such system may involve a medical device system that senses body signals of the patient—such as brain or cardiac activity shown in the figure—and analyzes those signals to identify one or more aspects of the signal that may identify the occurrence of a seizure. The signal may be processed to extract (e.g., mathematically by an algorithm that computes certain values from the raw or partially processed signal) features that may be used to identify a seizure when compared to the inter-ictal state. As shown in the right side of FIG. 2, the features may also be graphically displayed either in real time or subsequent to the event to enable visual confirmation of the seizure event and gain additional insight into the seizure (e.g., by identifying a seizure metric associated with the seizure).

A seizure metric as used herein refers to a quantitative, semi-quantitative, or qualitative value that indicates some aspect of a seizure event. Seizure metrics may be endogenous (derived from body signals of the patient that are associated with a seizure event) or exogenous (independent of body signals of the patient). Exogenous metrics may include, for example, the time of day at which a seizure event is detected, or a noise level, lighting condition, or other aspect of the patient's environment at the time of the seizure.

In some embodiments, the seizure metric may indicate how severe a seizure event is, e.g., by one or more of the magnitude and duration of the seizure effects on the patient's heart rate, EEG, body movements, responsiveness, blood pressure, temperature, etc., or by whether the seizure was accompanied by a fall. Seizure metrics indicating the severity of a seizure event are referred to herein as SSI metrics or indices, or more simply as SSI values or SSIs. In some embodiments, a seizure metric may indicate the time elapsed since a prior seizure event occurred, also known as an inter-seizure interval or ISI. In some embodiments, the seizure metric may indicate an impact that a seizure has on the patient, also referred to herein as a seizure impact or patient impact (PI). In some embodiments, a seizure metric may indicate other data associated with the seizure, such as whether the seizure event occurred at a particular time in the patient's circadian rhythm (e.g., the time of day or night the seizure occurred, whether the patient was awake or sleep, whether the patient was standing, sitting, or lying down, etc.).

A number of seizure metrics (e.g., one or more SSIs, ISIs, PIs, or other data such as time, posture, or patient environment data) may be used to characterize a particular seizure event. In some embodiments of the invention, a plurality of seizure metrics may be used as a matrix to characterize a seizure event, and a plurality of seizure events may be classified into one or more seizure classes. Seizure metrics may be stored in a memory of a medical device (MD) system, and in some embodiments may be transmitted to a user for analysis and/or display.

A patient may have certain kinds of seizures which may be classified as "extreme." Extreme seizures may be identified based on certain seizure metrics (e.g., SSIs, ISIs, PIs, time data, or other data). For example, a fall caused by a seizure may result in a skull fracture with brain laceration and/or hemorrhage, or a fracture of some other bone, resulting in a high patient impact (PI) value. Even if other seizure metrics (e.g., SSI or ISI values) might indicate a mild or non-extreme seizure, the patient impact (PI) may result in the seizure being classified as extreme in certain embodiments. Seizures may also cause other severe injuries such as burns or pulmonary edema. Similarly, extreme events may be characterized by low PI values but one or more high SSI or ISI values.

Seizure metrics in some embodiments refer to qualitative and/or quantitative data derived from body data recorded proximate (i.e., shortly before, during, or shortly after) a seizure. In some embodiments, seizure metrics may be derived from cortical electrical signals (e.g., total energy or maximum energy in the EEG signal from seizure onset to seizure end). In other embodiments, seizure metrics may be derived from non-cortical (e.g., non-EEG) autonomic signals, such as cardiac signals (e.g., increase or decrease in heart rate occurring during a seizure above baseline heart rate prior to the seizure, the heart rate increase/decrease above the baseline rate multiplied by the duration of the heart rate remaining above a baseline heart rate, area "below the curve" of heart rate versus time for the duration of the seizure). In still other embodiments, seizure metrics may be derived from accelerometer signals (e.g., acceleration and/or postural change indicative of a fall, maximum acceleration during a seizure, or duration of acceleration above a threshold), from electromotor (EMG) signals (e.g., maximum magnitude of a muscular contraction above a threshold value associated with normal physiological muscular contraction), or many other body signals such as body temperature, skin resistivity, and the like.

The body signals from which seizure metrics are determined may comprise one or more of autonomic (e.g., cortical electrical activity (EEG), heart beat, heart rate, heart rate variability, blood pressure, respiration, blood gases concentrations, or temperature), neurologic (e g, kinetic signals such as accelerometer signals and/or inclinometer signals), responsiveness/awareness (e.g., complex reaction time signals or test results), endocrine signals (e.g., hormone or neurotransmitter concentrations), metabolic signals (e.g., lactic acid concentrations or CK (creatine kinase) concentrations), and/or tissue stress marker signals.

Seizure metrics may include seizure severity indices (SSIs), inter-seizure intervals (ISIs, defined as the time (in seconds or minutes) elapsed between the onset of consecutive seizures), Patient Impact (PI) values (such as a value indicative of a broken bone or other injury to the patient as a consequence of the seizure), or other data associated with particular seizures (e.g., the time of day at which the seizure occurs, the time elapsed between a therapy administered to the patient and a seizure onset, whether a therapy was administered in response to the detection of the seizure). Information on determination of SSI, ISI, PI, and other seizure metrics are provided in parent U.S. application Ser. No. 12/896,525 filed Oct. 1, 2010, Ser. No. 13/098,262 filed Apr. 29, 2011, Ser. No. 13/040,996 filed Mar. 4, 2011, Ser. No. 13/091,033 filed Apr. 20, 2011, and Ser. No. 13/333,235 filed Dec. 21, 2011, each hereby incorporated by reference herein in its entirety.

In some embodiments, values of seizure metrics may be used to classify seizure events into one or more classes. In a particular embodiment, one seizure class may include at least one class of extreme seizure events. In one embodiment, extreme seizures may be identified as those seizures that are more than two standard deviations above the mean for SSI or ISI (e.g., seizures having a maximum HR more than two standard deviations greater than the mean reference, or having an ISI from a prior seizure less than two standard deviations below the mean reference, of all seizures under consideration in a group of seizures). Additionally, seizure metrics may include indications of the impact of a seizure on one or more body systems (e.g., neurology, cardiovascular, musculoskeletal systems, etc.). The seizure metric may be determined using other neurologic, autonomic, tissue stress markers, endocrine, metabolic, or musculo-skeletal signals or status, among others.

In some embodiments, seizure metric values may be used to classify certain seizures as non-extreme seizures, as tonic-clonic seizures, as simple partial seizures, as complex partial seizures, or many other types of seizures.

In some embodiments, patient seizure impact (PI) may be used to classify seizures as extreme. Seizures may be "extreme" regardless of SSI and/or ISI values, if they result in system dysfunction of a type, magnitude, duration and/or frequency exceeding the ictal or post-ictal baseline dysfunction for that subject, or if the seizure causes the subject to sustain injuries. In one embodiment, PI may be a scalar-valued function of one or more body data variables that simplifies a possibly complex set of body information down to a single number.

PI refers to effects of a seizure closely correlated in time with its occurrence. Measures of patient seizure impact (PI) collected over time may be used to determine patient seizure burden (PB), which is the cumulative effects of temporally close as well as remote seizures. PI and/or PB may provide information with regard to the effect of one or more seizures upon one or more parts of the body.

The PI may be a function of the health of a particular patient. In this manner, in one embodiment, the PI may reflect a more severe effect experienced by a first patient suffering a seizure of a first SSI, and reflect a less severe effect in a second patient who experienced a seizure of a second SSI, wherein the second SSI is substantially similar to the first SSI. The terms "patient impact", "seizure impact", and "patient seizure impact" may be used interchangeably herein and referred to as "PI". In one embodiment, the PI may be any statistic (or scalar-valued function) associated with a seizure that reflect some aspect of the seizure's impact. PI values and may be ordered/sorted or ranked so that the differences between different seizures can be measured, compared, and/or interpreted to provide meaningful information.

Classifying a seizure event as "extreme" may be based upon a deleterious impact upon (or seriousness in relation to) the patient's health (e.g., falls, bone fractures, cardiac and/or respiratory dysfunction, memory loss, etc.) and wellbeing (e.g., depression), or the condition of the patient's disease state (e.g., worsening of epilepsy). In different cases, extreme seizure events may be classified according to other standards as well, and need not necessarily be specifically limited to those described herein. Similarly, extreme seizure events may be a combination of the above described classifications. An extreme seizure event (e.g., status epilepticus, or a seizure causing a fall and head trauma) may result in coma, cardiorespiratory failure, metabolic acidosis, liver and/or renal failure, bed sores, bone fractures, tissue hypoxia, and/or brain damage.

In one embodiment, the approach of treating certain seizures as extreme events lends itself to a statistical or probabilistic approach for the prevention of status epilepticus through their anticipation or early detection.

More generally, seizures may be classified into a wide variety of classes including, by way of non-limiting examples: extreme & non-extreme seizures; generalized and partial seizures; tonic, tonic-clonic, absence, and other diagnostic classes; seizures caused by particular events (e.g., flashing lights as recorded by photometer, loud noises as detected by a microphone); seizures resulting in cardiac dysfunction (e.g., arrhythmias, EKG morphology changes, heart rate variability (HRV) changes, etc.); seizures having an abnormally long period of ictal impairment as measured by, e.g., one or more responsiveness/awareness tests; etc.

The following exemplary "seizure metrics" alone or in any combination may be used to classify a seizure or seizures in one or more seizure classes by quantifying one or more of the following:

1. Magnitude and/or rate of increase in seizure energy or intensity (EEG); seizure duration (from time of detection to seizure end time); extent of seizure spread (note that one type of seizure severity index may be derived from the values of at least two of these three metrics), seizure magnitude, rate of change (e.g., drop in energy from seizure to the post-ictal state), duration in post-ictal state energy compared to inter-ictal or ictal energy, and/or magnitude and rate of energy recovery from the post-ictal to the inter-ictal state; 2. Inter-seizure interval (time elapsed since the last seizure) duration; predicted ISI to the next seizure, including the conditional probability of time to the next seizure given the time elapsed since the last seizure; 3. Seizure frequency per unit time, cumulative intensity, duration, extent, spread, and/or seizure severity index (SSI) per unit time; 4. Cumulative magnitude, duration, and rate of the change in post-ictal energy per unit time compared to inter-ictal or ictal energy for the patient, and/or magnitude, rate, and extent of spread of changes in post-ictal energy compared to the inter-ictal or ictal states; 5. Magnitude, duration, and/or rate of change in level of consciousness (as measured, for example, using available coma scales such the Glasgow scale or qualitative classification (e.g., deep coma, superficial coma, stupor, lethargy, awake but confused)) as also used in clinical practice, compared to a baseline consciousness level; 6. Magnitude, duration (when applicable, e.g., when the patient is awake), and/or rate of change in one or more cognitive functions as measured, for example, using a reaction time (complex or simple) or any other validated neuropsychologic test; 7. Magnitude, duration, and/or rate of change in autonomic indices such as heart rate, heart rate variability, heart rhythm, EKG, EKG morphology (e.g., changes in one or more cardiac parameters such as the QRS complex, P waves, T waves, QT segment length, PQ segment length), blood pressure, respiration, catecholamines, temperature and/or galvanic skin resistance, among others; 6. Magnitude, duration, and/or rate of change in metabolic indices such as arterial pH, $SaO_2$, $CO_2$, glucose and/or electrolytes, among others; 7. Magnitude, duration, and/or rate of change in endocrine indices such prolactin, cortisol, and/or growth hormone, among others; and 8. Magnitude, duration, and/or rate of change in tissue stress markers, such as Reactive oxygen and nitrogen species, including but not limited to iso- and neuro-prostanes and nitrite/nitrate ratio, glutathione, glutathione disulfide, and glutathione peroxidase activity, citrulline, protein carbonyls, thiobarbituric acid, the heat shock protein family, catecholamines, lactic acid, N-acetylaspartate, free radicals, CK, Aldolase, troponin, and/or the like, or of their metabolites, when applicable.

Additional seizure metrics may also be used in certain embodiments of the present invention to classify seizure events, including time of day at seizure onset, seizure end, and/or inter-ictal state end, state of the patient (awake vs. asleep) at seizure onset, level of physical activity at the time the measurements were made, or patient age, gender, and/or health status.

In one or more embodiments, signals or index values indicative of one or more of autonomic, neurologic, endocrine, metabolic, and gastro-intestinal system function, or of tissue/organ stress, such as those listed below, along with processes and tools for measuring and/or deriving these signals and markers, may be used to derive one or more seizure metrics, which may in turn be used to classify seizures into one or more seizure classes:

I. Autonomic
  a) Cardiac: phonocardiogram (PKG) values, Echocardiography values, Apexcardiography (ApKG) values, intracardiac pressure, cardiac volume, the ratio of intra-cardiac pressure to cardiac volume, ejection fraction, blood flow, cardiac thermography, heart rate (HR), heart rate variability (HRV), rate of change of heart rate or HRV, heart sounds, heart rhythm, heartbeat wave morphology, thoracic wall deflection;
  b) Vascular: arterial pressure, arterial and/or venous blood wave pressure morphology, arterial and/or venous blood flow velocity, arterial and/or venous blood flow sounds, arterial and/or venous thermography;
  c) Respiratory: tidal volume, minute volume, respiratory wave morphology values, respiratory sounds, intercostalelectromyography (EMG), diaphragmatic EMG, at least one chest wall and/or abdominal wall motion, change of RR, rate of change of RR, arterial gas concentrations, oxygen saturation, end-tidal $CO_2$, blood pH;
d) Dermal: skin resistance, skin temperature, skin blood flow, sweat gland activity;
e) Neurotransmitters: concentrations of catecholamines and/or catecholamine metabolites, acetylcholine and/or acetylcholinesterase activity in blood and/or saliva, rate of change cathecholamines, acetylcholine and/or acetylcholinesterase activity;

II. Neurologic
a) Cognitive/Behavioral: level of consciousness, level of attention, reaction time, memory, visuo-spatial, language, reasoning, judgment, calculations, auditory and/or visual discrimination;
b) Kinetic: force of contraction, body movement direction, speed, acceleration, trajectory in one, two and/or three dimensions, pattern and/or quality, posture, orientation, position, body part orientation and/or position in reference to each other, body part orientation and/or position in reference to one or more predetermined axes or fiducials, muscle tone, agonist-to-antagonist muscle tone relation, gait, accessory movements, falls;
c) Vocalizations: formed and/or unformed vocalizations;
d) Electroencephalography (EEG)/Electrocorticography (ECoG), evoked potentials, field potentials, single unit activity;

III. Endocrine
a) prolactin, luteinizing hormone, follicle stimulation hormone, growth hormone, ACTH, cortisol, vasopressin, beta-endorphin, beta, lipotropin, corticotropin-releasing factor (CRF);

IV. Tissue Stress Markers
a) reactive oxygen and/or nitrogen species from the list comprising iso- and neuro-prostanes and nitrite-nitrate ratio, glutathione, glutathione disulfide and glutathione peroxidase activity, citrulline, protein carbonyls, thiobarbituric acid, a heat shock protein family, catecholamines, lactic acid, N-acetylaspartate, metabolites of citrulline, protein carbonyls, thiobarbituric acid, a heat shock protein family, catecholamines, lactic acid, N-acetylaspartate;

V. Metabolic:
a. arterial pH, arterial gases, lactate-pyruvate ratio, electrolytes and glucose; and/or VI. Musculo-Skeletal:
a. muscle mass, bone mass, bone density, bone fractures.

In human patients with pharmaco-resistant seizures, the probability density functions of energy and inter-seizure intervals of seizures originating from discrete brain regions may be partly described by power laws. The probability density function of seizure energy, a power law, differs from a Gaussian or normal probability density function in its skewness (to the right with respect to the mean), reflecting the presence of events with very large ("extreme") energy. For example, if seizure energy or severity is above two standard deviations from the mean (calculated from a normalized distribution), the seizure is considered as an extreme event, including but not limited to, status epilepticus, a risk of status epilepticus, an increased risk of status epilepticus, a risk of SUDEP, or an increased risk of SUDEP, and/or the like. Inter-seizure intervals with duration below two standard deviations to the left of the mean calculated from a normalized distribution may be indicative of an extreme epileptic event/state including but not limited to, status epilepticus, a risk of status epilepticus, an increased risk of status epilepticus, a risk of SUDEP, or an increased risk of SUDEP, and/or the like. Alternatively, an extreme event may correspond to that with severity as measured by any body signal, at or below the 10th percentile or at or above the 90th percentile of values, for the time of day (to account for circadian variability), or state (e.g., wakefulness versus sleep) or level of physical activity (moving about versus resting) and patient are classified as extreme. Other values for classification of events may be chosen as needed to improve performance. It should be noted, however, that in one or more embodiments no formal statistical analysis needs to be made to have extreme event(s); statistical significance is not necessarily needed to reach a conclusion that an extreme event has occurred.

With respect to extreme seizure events and/or patient mortality, status epilepticus (SE) may be an independent predictor of death. As compared with a first brief epileptic seizure, a first SE episode seems to increase the risk of developing epilepsy. Where prior studies incorrectly focused exclusively on seizure duration as an indicator of patient risk, a more useful and correct approach would also include a seizure severity index (SSI), calculated based on at least one of the autonomic, neurologic, endocrine, or metabolic indices, or tissue stress markers.

For example, heart rate, an autonomic index, may be used to compute a seizure severity index. In one example, a patient's mean interictal (in-between seizures) heart rate prior to a seizure is 80. Peak ictal heart rate for the seizure is 150 bpm, and the ictal increase in heart rate lasts for 40 sec. SSI may be calculated as either 6000 if the peak heart rate and seconds are used (150 bpm×40 sec), 100 if peak HR and minutes are used (150 bpm×⅔ min), 2800 if the net HR increase and seconds are employed ([150 bpm−80 bpm]×40 sec), or 46.67 if net HR increase and minutes are employed ([150 bpm−80 bpm]×0.67 min). Different but equivalent measures may be used by employing different units of time (e.g., seconds, minutes or hours).

In another embodiment, the "area under the curve" (rather than peak HR or net increase in HR over the duration of the seizure) may be also utilized to compute a particular SSI. Such an SSI indication may be used in some embodiments to take into account differences in a) the rates of increase in HR during seizures and non-seizure (e.g., exertional) tachycardia, and b) differences in the rate of HR return to the interictal baseline following a seizure in contrast to HR decrease following exertion (e.g., exercise) or postural changes (e.g., standing from a lying or sitting position). In other embodiments, measures such as the time from the detection of seizure onset to the peak HR during the seizure, and the time from peak HR during the seizure to the return to interictal baseline (or to within a desired percentage, e.g., 110% of the interictal baseline HR) may also be used as SSI indices.

As another example, blood oxygen saturation (SaO2) may be used to compute a seizure severity index. If a patient's mean interictal oxygen saturation during wakefulness is 93%, and during a convulsion it drops to a minimum of 60%, remaining below the interictal baseline for 60 sec., SSI values based on this index, may be 36 (0.60 minimum SaO2 during the seizure×60 seconds seizure duration), or 19.8 ([93% baseline SaO2−60% minimum ictal SaO2 during seizure]×60 seconds seizure duration) if the net decrease in ictal SaO2 from baseline SaO2 is used. Equivalent measures may of course be obtained by using different units of time (e.g., minutes instead of seconds for seizure duration) or SaO2. Similar to the "area under the curve" described above for HR, the "area under the curve" for SaO2 during a seizure may also be used to obtain SSI measures that take into account how fast SaO2 falls below, and returns to, the interictal baseline during and after the seizure. Additionally, the elapsed time for SaO2 to fall from the interictal baseline to the minimum SaO2 during the seizure, as well as the time required for SaO2 to return to interictal baseline from the minimum ictal SaO2 value, may also be used as SSI indices.

In one embodiment, seizure severity index (SSI) values indicative of the severity of a seizure may be determined based upon body data as described above. In one embodiment, the determined SSI value(s) may be compared to reference/extreme reference values that may or may not include a status epilepticus value. The status epilepticus value(s) may be based upon at least one of a past SSI value, a mean SSI value, a median SSI value, a mode SSI value, a percentile SSI value, a normalized SSI value, a distribution of SSI values, or to any other statistical transformation of an SE index or observable SE index change.

The increased probability of subclinical and clinical pharmacoresistant seizures to occur closely spaced in time (i.e., in temporal clusters), an observation previously made for clinical seizures only, as well as the decreasing probability of seizure occurrence as the time since the last seizure increases, may be interpreted as: (i) reflecting the inherent capacity of seizures to trigger other seizures; (ii) indicating some form of seizure interdependency or plasticity ("memory") in the system; and/or (iii) a clinically useful observation that in the embodiments disclosed herein may be exploited to anticipate and prevent extreme epileptic events, including but not limited to status epilepticus.

In some embodiments, the present invention determines one or more data points associated with an event detected from body data of an epilepsy patient. In some cases the data points may be seizure metric data values associated with a seizure, and the seizure may be classified into one or more seizure classes based upon the seizure metrics. Seizure metric data may be used to classify the seizure based upon 1) data associated with the seizure itself, or 2) based upon data not directly related to the seizure, but associated with the seizure event (e.g., data from the patient's environment such as sound, noise, temperature, or humidity, or patient-specific data such as level of fitness, fatigue, etc.). In some cases, the data associated with the event may indicate that the patient has had a seizure that has resulted in unforeseen and/or atypical or undesirable (negative) consequences for the patient. Such events may include, by way of non-limiting examples, a fall resulting in a broken bone or metabolic derangement (transient severe metabolic acidosis, or a worsening of autonomic function (e.g., decrease in heart rate variability)) over time such that the patient's risk profile for one or more adverse events has increased, given the patient's seizure type.

While status epilepticus is one example of an extreme event, many other events that an epileptic patient may have may also present an elevated risk to health or safety, and may also be classified as extreme events. Accordingly, it will be appreciated that the terms "status epilepticus," "extreme event," and "extreme seizure" are not synonymous, although they may in some instances be used herein in reference to the same event. Some embodiments of the present invention use neurologic and other types of body signals (e.g., autonomic, metabolic) in a multi-variant, adaptive manner to optimize sensitivity and specificity of detection of SE and CSE, and more importantly to anticipate SE and CSE and also SUDEP.

The invention also broadens diagnostic and therapeutic horizons by extending the concepts of extreme seizure and epileptic events to phenomena other than generalized or partial status epilepticus and sudden death. In some embodiments, the present invention involves quantifying the impact of status epilepticus on one or more body systems to either 1) prevent bodily functions from entering the extreme state (thus becoming extreme epileptic events) or 2) provide early treatment to minimize the risk of mortality.

In some embodiments, the present invention involves detecting a plurality of seizure events based upon one or more body systems affected by a seizure, and performing a classification analysis by classifying the seizure events into one or more classes. In particular embodiments, the classification analysis may be repeated as additional seizures are detected, and changes in the seizure classes over time may be identified. Changes in seizure classes may, in turn, be used to perform a number of tasks, such as identifying extreme (and by extension, non-extreme) epileptic events, and identifying changes in the patient's disease state (e.g., whether the patient's epilepsy is improving, worsening, remaining the same, improving in some aspects but worsening in others, etc.).

In one more embodiments, the invention comprises a method identifying a plurality of seizure events, determining one or more seizure metric values for each of the seizures, performing a classification analysis of each of the plurality of seizure events, identifying one or more additional seizure events, determining one or more seizure metric values for each of the additional seizure events, performing a second classification analysis, comparing the results of the first and second classification analyses, and taking one or more actions in response to the comparison of the first and second classification analyses. The responsive action(s) may comprise one or more of reporting a change in one or more classes from the first classification analysis to the second classification analysis, reporting the absence of such a change, displaying a resulting of the first or second classification analyses or the comparing, identifying a new class based on the comparing, identifying the disappearance of a class, identifying one or more outlier seizure events, identifying an effect of a therapy, providing a therapy in response to the comparing, identifying a proposed change in therapy, identifying a proposed additional therapy, or identifying an extreme seizure event.

Electrocardiography (ECG) indicators of pathologic cardiac repolarization, such as prolongation or shortening of QT intervals as well as increased QT dispersion, are established risk factors for life-threatening tachyarrhythmia and sudden death. Abnormalities in cardiac repolarization have recently been described in people with epilepsy. Importantly, periictal ventricular tachycardia and fibrillation have also been reported in the absence of any underlying cardiac disease. Based on these abnormalities in cardiac repolarization, measures to reduce the risk of, or prevent, sudden death may include anti-arrhythmic medication and implantation of cardiac combined pacemaker-defibrillator devices.

Seizures are powerful biological stressors and inductors of stress marker indices and deplete the body of certain antioxidants, such as glutathione peroxidase. Exemplary stress marker indices comprise changes (direction, rate, or magnitude) in glucose, prolactin, cortisol, catecholamines, chromogranin A, free radicals or reactive oxygen species, lactic acid, blood gases, N-acetylaspartate, in the expression of heat shock proteins, or in metabolites of any or all thereof. For example, a "cortisol parameter" refers to a stress marker index relating to cortisol or a metabolite thereof, and a "catecholamine parameter" refers to a stress marker index relating to a catecholamine or a metabolite thereof. The concentration of certain compounds that protect from biological stress (e.g., dehydroepiandrosterone or its sulfate conjugate, glutathione peroxidase) or the body's total antioxidant capacity may be also measured to determine if it is adequate and if not to increase it using commercially or naturally available antioxidants to stall disease progression. Stress marker index indices and antioxidants may be measured in brain (invasively and/or non-invasively), CSF, plasma, serum, erythrocytes, urine, and saliva (e.g. alpha amylase).

Although not so limited, methods and apparatus capable of implementing embodiments of the present invention are described below. In the context of this description, a medical device or medical system may be referred to as an implantable medical device and/or an implantable medical device/system (IMD). It is contemplated that such a device and/or system may be implantable or non-implantable/non-implanted in various embodiments without departing from the spirit and scope of the invention. That is, when an implantable medical device/system (IMD) is described in one or more embodiments, it is also contemplated that a corresponding non-implanted or non-implantable may be used in one or more alternate embodiments.

FIG. 1 is a block diagram depiction of a medical device (MD) 100, in accordance with an illustrative embodiment of the present invention. The MD 100 may be fully implantable (such as an implantable vagus nerve stimulation system, or deep brain stimulation system) in some embodiments, and fully or partially external to the patient's body in other embodiments.

The MD 100 may comprise a controller 110 capable of controlling various aspects of the operation of the MD 100. The controller 110 may include a processor 115, a memory 117, as well as other common circuits associated with processors and integrated circuits (e.g., A/D converters, digital signal processors, etc.) for processing and storing data. Processor 115 may comprise one or more microcontrollers, microprocessors, or equivalent circuitry capable of performing various executions of software and/or firmware. Memory 117 may store various types of data (e.g., internal data, external data instructions, software codes, status data, diagnostic data, etc.), and may include one or more of random access memory (RAM), dynamic random access memory (DRAM), electrically erasable programmable read-only memory (EEPROM), flash memory, etc. Memory 117 may be separate from, but communicatively coupled to the controller 110 in some embodiments (as shown in dotted line form in FIG. 1), or may be integrated into controller 110 and/or processor 115.

The MD 100 may also comprise a power supply 130, which may comprise a battery, voltage regulators, capacitors, etc., to provide power for the operation of the MD 100, including delivering the therapeutic electrical signal. The power supply 130 in some embodiments may be rechargeable, while in other embodiments it may be non-rechargeable. The power supply 130 provides power for the operation of the MD 100, including electronic operations and the electrical signal generation and delivery functions. The power supply 130 may comprise a lithium/thionyl chloride cell or a lithium/carbon monofluoride (LiCFx) cell if the MD 100 is implantable, or may comprise conventional watch or 9V batteries for external (i.e., non-implantable) embodiments. Other battery types known in the art of medical devices may also be used.

The MD 100 may include one or more sensors 112 for sensing one or more body data streams in some embodiments. The sensor(s) 112 are capable of receiving signals related to a body parameter, such as the patient's heart beat, and delivering the signals to the MD 100. In one embodiment, the sensor(s) 112 may be implanted, such as electrode(s) 106, 108. In other embodiments, the sensor(s) 112 are external structures that may be placed on the patient's skin, such as over the patient's heart or elsewhere on the patient's torso. In some embodiments, lead 111 may be omitted and the MD 100 may communicate wirelessly with sensor 112. Various types of body data, such as cardiac data, respiration data, body motion or movement data, etc., may be provided by sensors 112. Controller 110 may be capable of receiving and/or processing body data received from sensors 112. Processor 115 may receive body data from one or more modules or units within MD 100, may process the received data, and may provide data to one or more modules or units within MD 100. In some embodiments, processor 115 may be integrated with one or more other units or modules of MD 100, described hereinafter.

In one embodiment, body data may be provided (e.g., from processor 115, memory 117, and/or sensors 112) to a body index determination unit 121, which may determine one or more body indices from the provided body data. In one embodiment, body index determination unit 121 may determine one or more body indices that may be indicative of a seizure event. For example, body index determination unit 121 may calculate or more autonomic, neurologic, metabolic, tissue, or tissue stress indices that may be compared to corresponding thresholds to determine the onset of a seizure. Additional details regarding seizure detection using one or more body indices are provided in the parent applications to the present application, as referred to earlier. In one embodiment, a seizure determination unit 123 may determine whether or not a seizure event has occurred using one or more body indices determined by the body index determination unit 121.

Embodiments of the present invention also involve characterizing seizure events by determining one or more seizure metrics, and classifying a plurality of seizure events into classes based upon the seizure metrics. Referring again to FIG. 1, when a seizure event has been identified, body data may be provided (e.g., from processor 115, memory 117, and/or sensors 112) to a seizure metric determination unit (SMDU) 125 to determine one or more seizure metric values associated with the seizure event. In one embodiment, processor 115 may also provide additional data (e.g., time data, sound or environmental data) to SMDU 125, which may determine seizure metric values that are derived in whole or in part from non-body data. SMDU 125 may store the seizure metric data in memory 117.

A variety of seizure metrics may be determined by MD 100 and used to characterize seizure events. SMDU 125 may comprise one or more sub-units to determine different kinds of seizure metrics. In one embodiment, SMDU 125 includes a seizure severity index unit (SSIU) 126. SSIU 126 may identify one or more SSI values for a plurality of seizure events, and may store those values in memory 117 for reporting to a user (e.g., through a monitoring unit 170). SMDU 125 may also comprise an Inter-Seizure Interval Unit (ISIU) 127, which may determine one or more time periods between the detected seizure and a prior seizure event. Details on determining SSI and ISI values are provided in parent U.S. application Ser. Nos. 13/040,996 and 13/333,235. SMDU 125 may further include a patient seizure impact (PIU) 128 to identify seizure metrics indicative of a patient impact index. In some embodiments, SMDU 125 may also include a time of occurrence unit (TOU) 129 to identify a time of occurrence of the seizure. In one embodiment, TOU 129 may be part of ISIU 127. Additional sub-units of SDMU may also be provided to determine additional seizure metric values, which may include, for example, sensors or transmitters/receivers to obtain data relating to the patient's environment, location, quality of life (QOL) measures, etc.

In one aspect, the SMDU may comprise a SSIU 126 which may be used to determine, from body data, one or more indices that describe or characterize a severity measure of a seizure event. SSIs may be calculated in some embodiments using one or more of a seizure intensity measure, a seizure duration measure, and an extent of seizure spread measure based on one or more of autonomic, endocrine, metabolic, tissue stress marker signals. For example, SSI may be the product of a seizure intensity measure and a seizure spread measure, or the sum of a seizure intensity, seizure duration, and seizure spread measure from one or more of the signals previously mentioned. An SSI may be a scalar-valued function of one or more body data variables that simplifies a possibly complex set of body information down to a single number. An SSI may be any statistic (or scalar-valued function) associated with a seizure with the property values that reflect some aspect of the severity of the corresponding seizures and may be ordered/sorted so that the distance between the SSI values for different seizures can be measured, compared and/or interpreted to provide meaningful information.

In one embodiment, the SSI may be a quantity whose variation over a period of time measures the change in some body data or body phenomenon. The SSI may also be a statistic associated with the seizure that enables comparison between different seizures. The values for different seizures may be ordered/sorted or ranked and the distance (in a Euclidian or non-Euclidian sense) between them may be measured/compared/interpreted to provide meaningful information. If the SSI values describe the severity of the seizure not in absolute terms, but in a manner relative to other seizures for that patient (or relative to other patients), the SSI may be referred to as a "Relative SSI." In some embodiments, when more than one SSI is used at the same time, the plurality of SSIs may be combined into a single SSI by weighted averaging, and/or the like.

In one embodiment, SMDU 125 may include an interseizure interval unit (ISIU) 127. The ISIU 127 may determine an index based upon inter-seizure intervals between one or more seizures experienced by the patient. The inter-seizure interval index may, in some embodiments, be representative of the current inter-seizure interval relative to a past seizure event. This may comprise the immediately preceding seizure or the nearest seizure within the same class as the present seizure. ISIU 127 may determine an ISI value in real-time or off-line after the seizure event has occurred. ISIU 127 may determine ISI values based upon body data information, external indications (e.g., the patient's environment or surroundings), a patient's past seizure data, a normalized seizure data distribution, expected seizure data, and/or other data that would become apparent to one of skill in the art having the benefit of this disclosure.

In some embodiments, SDMU 125 may comprise a patient seizure impact unit (PIU) 128, which determines an impact of the seizure on a patient. PIU 128 may determine a number of measures indicative of the impact of a particular seizure on one or more systems of the patient's body. This may include cognitive test results, severity measures (e.g., maximum acceleration) associated with falls, indications of effects on cardiac function such as tachycardia, bradycardia, or asystole, effects on breathing such as apnea periods. Trauma may also be determined by, for example, a detected hard fall as measured by an accelerometer followed by one or more of an extended period in which the patient remains prone, a period of asystole, or a period of apnea. PIU 128 may also determine other indications of trauma such as burns, broken bones, etc.

Time of Occurrence Unit (TOU) 129 may comprise software, hardware, firmware, etc., that determines a time at which seizure determination unit 123 identified the occurrence of a seizure. TOU 129 may provide one or more of a time of day (e.g., 2:22:14 PM) of the seizure, a month, date and year the seizure occurred, as well as patient-specific measures such as how long the patient had been awake, upright, sleeping, reclining, etc. at the time of the seizure. Data from TOU 129 may be used, for example, to identify seizure triggers, periods of increased or decreased risk of seizures, or to identify other temporal variables affecting the patient's disease state.

MD 100 may further comprise a seizure classification analysis (SCA) unit 140 which may classify a plurality of seizures based upon the proximity of the seizures to one another in a seizure metric phase space. Such classifications based on the similarity of seizure in terms of one or more seizure metrics (e.g., SSI, ISI, PI, time of occurrence, etc.) may be an alternative to classifications based on pre-existing criteria independent of proximity in the seizure metric phase space. In one embodiment, SCA unit 140 may create a multidimensional matrix for each seizure from seizure metric values associated with that seizure, and the classification analysis may comprise an n-dimensional analysis using n seizure metrics associated with the plurality of seizures. The analysis may comprise identifying one or more groups of seizures based on their proximity to each other in the n-dimensional seizure phase space. Different analyses may be performed by selecting different seizure metrics for each of the dimensions in the n-dimensional space. In one embodiment the multidimensional matrix comprises an m-dimensional matrix, where m and n may be different and analyses may be performed by selecting n dimensions, corresponding to n seizure metric data points, within the m-dimensional matrix space maintained for the seizures.

In one embodiment, the SCA unit 140 may classify a plurality of seizure events into one or more classes based on the seizure metric data determined by SMDU 125. In one embodiment, the one or more classes into which each of the plurality of seizure events may be classified may be clinical seizure classes, e.g., simple or complex partial seizures, primarily or secondarily generalized seizures, tonic seizures, tonic-clonic seizures, etc. In one embodiment, the one or more classes may correspond to patient risk levels, e.g., mild seizure events or extreme seizure events. In still other embodiments, the one or more classes may correspond to particular seizure metrics, or combinations of seizure metrics, such as seizures accompanied by tachycardia, breathing changes, temperature changes, or seizures occurring in a particular time of day (e.g., late morning, early afternoon, during sleep, etc.).

In some embodiments, SCA unit 140 may perform a seizure classification analysis in real time as seizure events are detected. In other embodiments, the classification analysis may be performed off-line on stored seizure metric data. In one embodiment, SCA unit 140 may perform a first seizure classification on a plurality of seizure events at a first point in time. As additional seizures are detected, additional seizure metric data may be determined by SMD unit 125 for the additional seizures. SCA unit 140 may subsequently perform a second seizure classification analysis at a second point in time after the first seizure classification analysis. The second seizure classification analysis may be performed using seizure metric data on the seizures analyzed in the first analysis as well as on one or more additional seizures occurring after the first seizure analysis.

In still further embodiments, SCA unit 140 may perform a first seizure classification analysis on a plurality of seizures for a first defined time period, e.g., for all seizures occurring in a particular week, month, quarter, year, etc. SCA unit 140 may further perform a second seizure classification analysis on a second plurality of seizures for a second time period. The second time period may include a time period occurring entirely after the first defined time period. In another embodiment, the second time period may include all or part of the first time period as well as an additional time period after the first time period.

In some embodiments, SCA unit 140 may be programmed to perform a seizure classification analysis at pre-specified intervals. SCA unit 140 may alternatively perform a seizure classification analysis in response to request for such an analysis by a user, or by the occurrence of a particular event, e.g., by a seizure metric determination indicating that the patient has experienced a severe seizure.

MD 100 may further comprise a classification analysis comparator (CAC) 142. CAC 142 may compare a first classification analysis to a second classification analysis and identify changes, differences, trends, or other measures of contrast between the first and second analyses. The differences may in one embodiment include a change in a seizure class from the first analysis to the second analysis. Changes may include, e.g., that the class identified in the first analysis has grown, shrunk, increased or decreased in density, elongated, shifted in centroid, or has changed in other aspects that may be mathematically and/or graphically identified. In one embodiment, the first and second time periods may be non-overlapping time periods, and the CAC 142 may identify whether a seizure class in the first time period is present in the second time period. The CAC 142 may further indicate change or trend in the patient's disease state from the first to the second time period.

In another embodiment, CAC 142 may, as a result of the comparison of the first classification analysis and the second classification analysis, determine that there are no significant differences between the first and second analyses. In a still further embodiment, CAC 142 may compare a first and a second classification analysis and identify the emergence of a new class in the second analysis that was not present in the first analysis, or the disappearance in the second analysis of a class identified in the first analysis. CAC 142 may also identify one or more outlier seizure events that are not part of any class, and may identify extreme seizure events, including but not limited to sub-classes of extreme events. In another embodiment, the CAC 142 may identify an effect of a therapy, or may identify additional therapies that may be proposed. Output values of CAC 142 may be stored in MD 100 in memory 117 or other storage areas.

MD 100 may further comprise a communication unit 160 that may facilitate communications between MD 100 and various other devices. In particular, communication unit 160 is capable of transmitting and receiving signals to and from a monitoring unit (MU) 170, such as a handheld computer, PDA or tablet that can communicate with the MD 100 wirelessly or by cable. Communication unit 160 may include hardware, software, firmware, or any combination.

MU 170 may receive, process, display, and/or respond to data from SCA unit 140 and/or CAC 142. In one embodiment, MU 170 may display one or more seizure metrics determined by SCA unit 140. In another embodiment, MU 170 may graphically present on a display 175 seizure metric data for at least a portion of the seizures in the first analysis and the second analysis to depict for a user a change in a seizure class over time.

In one embodiment, monitoring unit 170 may further comprise at logging/reporting module 165. The logging/reporting module 165 may be adapted to log and/or store data related to the patient, the patient's physical condition, the patient's disease and disease state and/or any other body data. The logging/reporting module 165 may store information relating to the patient's disease (e.g., seizure events, data related to time of recovery after seizure events and/or patient sleep cycles). The logging/reporting module 165 may also be adapted to log and/or store a timestamp indicative of the time and day on which stored data is/was acquired. The logging/reporting module 165 may be adapted to report stored data, or any portion thereof, to a patient, a physician, a care giver, an external computer, a database unit 150, a local database unit 155 and/or a remote device 192. In some embodiments, logging/reporting module 165 may be part of the MD 100 rather than monitoring unit 170, as depicted by dotted lines in FIG. 1.

In one embodiment, MD 100 may further include a responsive action unit 144 to perform a variety of actions in response to the SCA unit 140 or the CAC 142. Such actions may include, for example, reporting a change from the first classification to the second classification; reporting the absence of a change from the first classification to the second classification; displaying a result of at least one of the first classification analysis, the second classification analysis, or an output of CAC 142; identifying the emergence of a new class based on the CAC 142; identifying the disappearance of a prior class based on the comparing; identifying one or more outlier seizure events; identifying an effect of a therapy; providing a therapy to the patient; identifying a proposed change in therapy; identifying a proposed additional therapy; and identifying an extreme seizure event.

In one embodiment, responsive action unit 140 may include a therapy unit 120 to provide a therapy to the patient. In a particular embodiment, the therapy may include an electrical stimulation provided by a lead 101 to one or more electrodes 106, 108 coupled to a target tissue such as a brain area, a cranial nerve (e.g., a vagus, trigeminal, hypoglossal, or glosspharyngeal nerve), a spinal cord, a sympathetic nerve or ganglion, or a peripheral nerve. Controller 110 is capable of causing therapy unit 120 to provide a therapy in response to one or more of a programmed therapy, an event detected by seizure determination unit 123, or an output of SCA unit 140 or CAC 142. The therapy unit 120 may comprise various circuitries, such as electrical signal generators, impedance control circuitry to control the impedance "seen" by the leads, and other circuitry that receives instructions relating to the delivery of the electrical signal to tissue.

In addition to a therapy provided by therapy unit 120, controller 110 may cause MD 100 to take other responsive actions, and may send instructions to monitoring unit 170 to cause the monitoring unit or other units to take further responsive actions to, e.g., an event detected by seizure determination unit 123, or an output of SCA unit 140 or CAC 142. In one or more embodiments, the responsive action may comprise providing drug treatments, oxygen treatments, body or brain cooling and/or the like. For example, the controller 110 may receive manual instructions from an operator externally, or may cause an electrical signal to be generated and delivered based on internal calculations and programming. In other embodiments, the MD 100 does not comprise a therapy unit 120, lead assembly 122, or leads 101.

In some embodiments, an event or warning button may 135 may be provided to alert a patient and/or caregiver of the occurrence of an event or an output of a seizure classification analysis or comparison. As shown in FIG. 1, the event/warning button 135 may be a separate device from MD 100 and MU 170. In other embodiments, event/warning button 135 may be incorporated as part of MD 100 or MU 170.

An embodiment of a medical device adaptable for use in implementing some aspects of embodiments of the present invention is provided in FIG. 2. Details concerning FIG. 2 of the present application is provided in FIG. 2 of U.S. application Ser. No. 13/040,996 (filed Mar. 4, 2011), Ser. No. 13/091, 033 (filed Apr. 20, 2011), and Ser. No. 13/333,235 (filed Dec. 21, 2011), and in the discussion thereof. As previously noted, the foregoing applications are each incorporated by reference herein.

Figure 3:
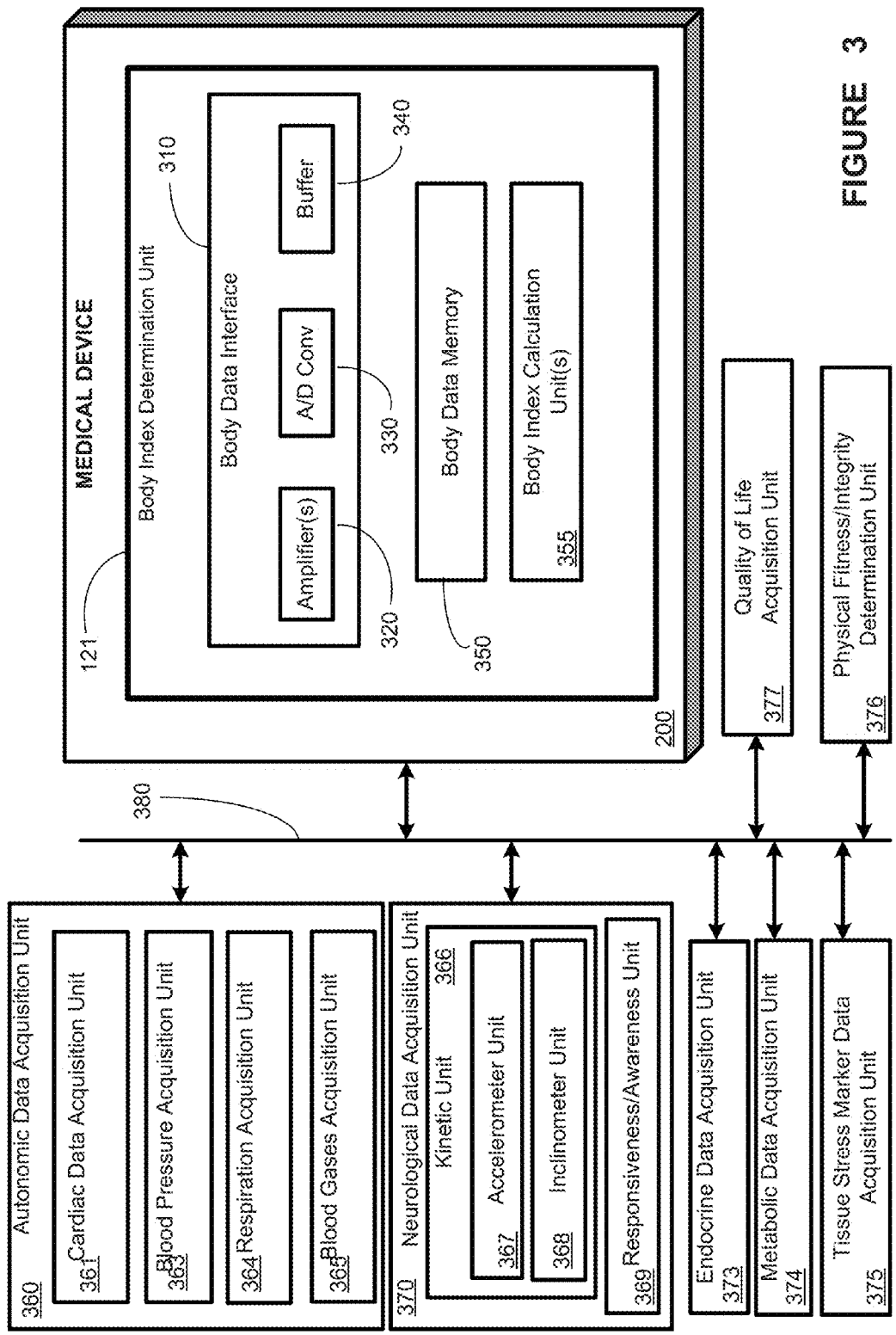
FIG. 3 provides a stylized diagram of a medical device and different data acquisition units that may provide output(s) used by a body index determination unit, in accordance with one illustrative embodiment of the present invention.

Turning now to FIG. 3, a block diagram depiction of an exemplary implementation of the body index determination unit 121 of FIG. 1 is shown. The body index determination unit 121 may include hardware (e.g., amplifiers, accelerometers), tools for chemical assays, optical measuring tools, a body data memory 350 (which may be independent of memory 117 or part of it) for storing and/or buffering data. The body data memory 350 may be adapted to store body data for logging or reporting and/or for future body data processing and/or statistical analyses. Body index determination unit 121 may also include one or more body data interfaces 310 for input/output (I/O) communications between the body index determination unit 121 and sensors 112. Body data from memory 350 and/or interface 310 may be provided to one or more body index calculation unit(s) 355, which may determine one or ore body indices.

In the embodiments of FIG. 3, sensors 112 may be provided as any of various body data units/modules (e.g., autonomic data acquisition unit 360, neurological data acquisition unit 370, endocrine data acquisition unit 373, metabolic data acquisition unit 374, tissue stress marker data acquisition unit 375, and physical fitness/integrity determination unit 376) via connection 380. Connection 380 may be a wired connection (e.g., lead 111 from FIG. 1) a wireless connection, or a combination of the two. Connection 380 may be a bus-like implementation or may include an individual connection (not shown) for all or some of the body data units.

In one embodiment, the autonomic data acquisition unit 360 may include a cardiac data acquisition unit 361 adapted to acquire a phonocardiogram (PKG), EKG, echocardiography, apexcardiography and/or the like, a blood pressure acquisition unit 363, a respiration acquisition unit 364, a blood gases acquisition unit 365, and/or the like. In one embodiment, the neurologic data acquisition unit 370 may contain a kinetic unit 366 that may comprise an accelerometer unit 367, an inclinometer unit 368, and/or the like; the neurologic data acquisition unit 370 may also contain a responsiveness/awareness unit 369 that may be used to determine a patient's responsiveness to testing/stimuli and/or a patient's awareness of their surroundings. Body index determination unit 121 may collect additional data not listed herein, that would become apparent to one of skill in the art having the benefit of this disclosure.

The body data units ([360-370], [373-377]) may be adapted to collect, acquire, receive/transmit heart beat data, EKG, PKG, echocardiogram, apexcardiogram, blood pressure, respirations, blood gases, body acceleration data, body inclination data, EEG/ECoG, quality of life data, physical fitness data, and/or the like.

The body data interface(s) 310 may include various amplifier(s) 320, one or more A/D converters 330 and/or one or more buffers 340 or other memory (not shown). In one embodiment, the amplifier(s) 320 may be adapted to boost and condition incoming and/or outgoing signal strengths for signals such as those to/from any of the body data acquisition units/modules (e.g., ([360-370], [373-377])) or signals to/from other units/modules of the MD 100. The A/D converter(s) 330 may be adapted to convert analog input signals from the body data unit(s)/module(s) into a digital signal format for processing by controller 210 (and/or processor 215). A converted signal may also be stored in a buffer(s) 340, a body data memory 350, or some other memory internal to the MD 100 (e.g., memory 117, FIG. 1) or external to the MD 100 (e.g., monitoring unit 170, local database unit 155, database unit 150, and remote device 192). The buffer(s) 340 may be adapted to buffer and/or store signals received or transmitted by the body index determination unit 121.

As an illustrative example, in one embodiment, data related to a patient's respiration may be acquired by respiration unit 364 and sent to MD 100. The body index determination unit 121 may receive the respiration data using body data interface(s) 310. As the data is received by the body data interface(s) 310, it may be amplified/conditioned by amplifier(s) 320 and then converted by A/D converter(s) into a digital form. The digital signal may be buffered by a buffer(s) 340 before the data signal is transmitted to other components of the body index determination unit 121 (e.g., body data memory 350) or other components of the MD 100 (e.g., controller 110, processor 115, memory 117, communication unit 160, seizure determination unit 123, or seizure metric determination unit 125 or its sub-units, or the like. Body data in analog form may be also used in one or more embodiments.

Body index determination unit may 121 may use body data from memory 350 and/or interface 310 to calculate one or more body indices in body one or more body index calculation unit(s) 355. A wide variety of body indices may be determined, including a variety of autonomic indices such as heart rate, blood pressure, respiration rate, blood oxygen saturation, neurological indices such as maximum acceleration, patient position (e.g., standing or sitting), and other indices derived from body data acquisition units 360, 370, 373, 374, 375, 376, 377, etc.

Turning now to FIG. 4, an MD 100 (as described in FIG. 3) is provided, in accordance with one illustrative embodiment of the present invention. FIG. 4 depicts the body data acquisition units of FIG. 3, as in accordance with one embodiment, included within the MD 100, rather being externally coupled to the MD 100, as shown in FIG. 3. In accordance with various embodiments, any number and type of body data acquisition units may be included within the MD 100, as shown in FIG. 4, while other body data units may be externally coupled, as shown in FIG. 3. The body data acquisition units may be coupled to the body index determination unit 121 in a fashion similar to that described above with respect to FIG. 3, or in any number of different manners used in coupling intra-medical device modules and units. The manner by which the body data acquisition units may be coupled to the body data collection module 275 is not essential to, and does not limit, embodiments of the instant invention as would be understood by one of skill in the art having the benefit of this disclosure. Embodiments of the MD depicted in FIG. 4 may be fully implantable or may be adapted to be provided in a system that is external to the patient's body.

As shown in FIG. 1, MD 100 in some embodiments may include a seizure metric determination unit 125 to determine one or more types of seizure metrics. Various subunits may be provided to determine different seizure types of seizure metrics, e.g., seizure severity indices determined by SSIU 126, inter-seizure intervals determined by ISIU 127, patient seizure impact determined by PIU 128, and time of occurrence determined by TOU 129.

Figure 5A:
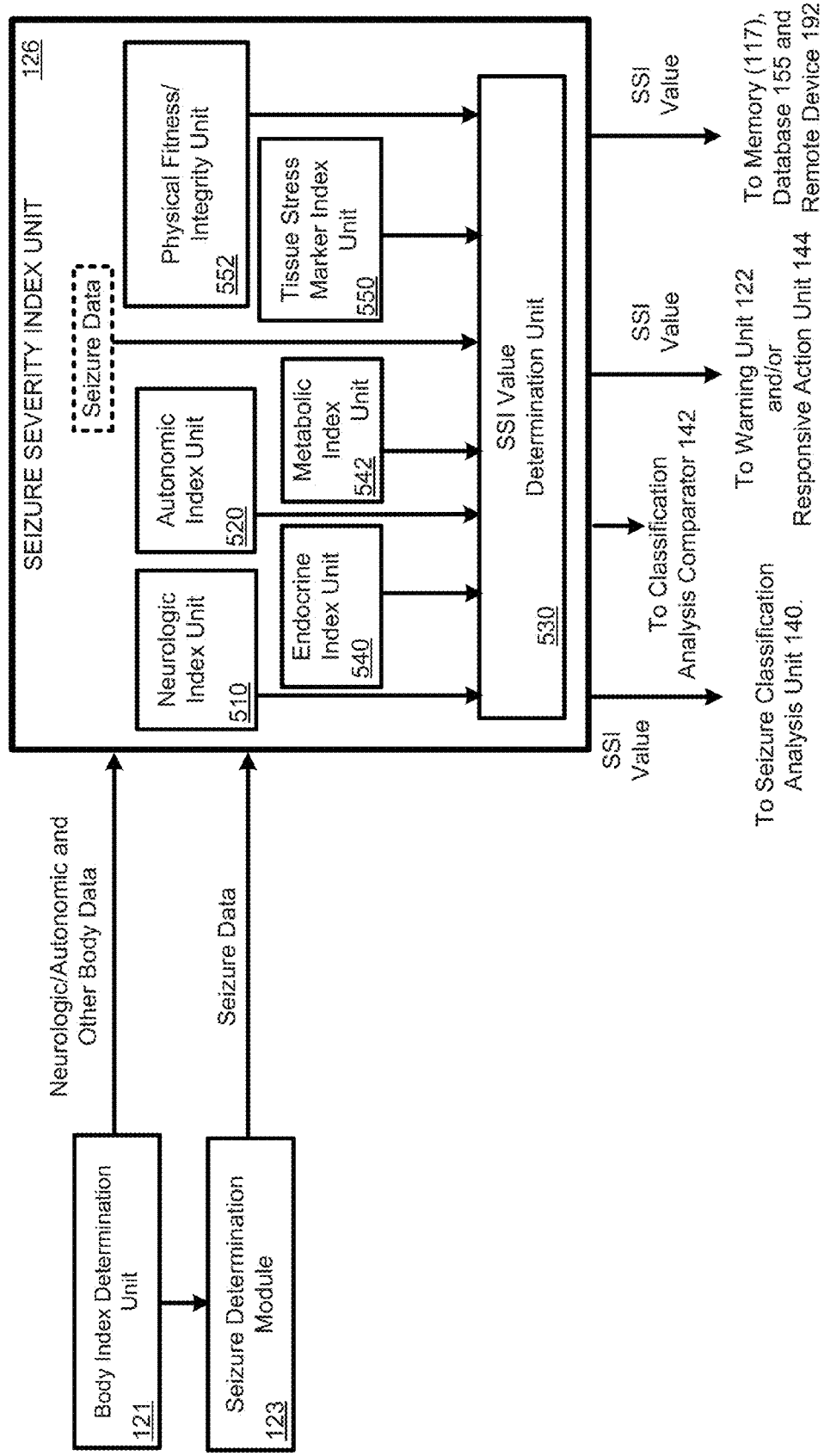
FIG. 5A provides a stylized diagram of a seizure severity index unit for determining a seizure severity index using body data and/or seizure data, in accordance with one illustrative embodiment of the present invention.

Turning now to FIG. 5A, a block diagram depiction of a seizure severity index unit (SSIU) 126 is provided, in accordance with one illustrative embodiment of the present invention. In one embodiment, the SSIU 126 may be adapted to determine a seizure severity index (SSI). The SSI unit 126 may use body data (e.g., from data acquisition units 360, 370, 373, 374, 375, 376, 377 shown in FIG. 3), body index data (e.g., from body index determination unit 121) and/or seizure data from determination unit 123. One or more subunits may be provided in SSIU 126 to determine different kinds of seizure severity indices. Data from various body index and/or data units may be provided to an SSI value determination unit 530, which, together with information from seizure determination unit 123 (e.g., indicating that a seizure has occurred), is used to determine one or more seizure severity indices.

In one embodiment, data is provided to SSI value determination unit 530 from one or more body index units such as neurologic index unit 510, autonomic index unit 520, endocrine index unit 540, metabolic index unit 542, tissue stress marker index unit 550, and/or physical fitness/integrity unit 552, as well as seizure data (e.g., from seizure determination unit 123). SSI value determination unit 530 may determine a number of different seizure severity indices based upon the information provided, including autonomic indices relating to the severity of the seizure event, such as the maximum heart rate during the seizure, the time elapsed from detection of the seizure to the maximum heart rate, the rate of change of heart rate from a baseline heart rate at the time of seizure detection until the maximum seizure heart rate, the time required for heart rate to return to baseline (measured from, e.g., the time of seizure detection, the time of maximum HR during the seizure, or another reference time), the rate of change of heart rate during the return to baseline, etc. In addition to the foregoing cardiac-based seizure severity indices, a variety of neurologic indices may be determined from kinetic data such as a triaxial accelerometer or inclinometer, including the maximum acceleration recorded during the seizure, the duration of non-physiologic movements (e.g., pathological movements associated with a convulsive seizure, whether the patient's posture changed (e.g., from a fall) during the seizure.

The neurologic index unit 510, autonomic index unit 520, endocrine index unit 540, metabolic index unit 542, stress marker index unit 550 and/or physical fitness/integrity unit 552 may be adapted to transmit their respective index values to an SSI value determination unit 530. The SSI value determination unit 530 may determine one or more of a neurologic index value, an autonomic index value, an endocrine index value, a metabolic index value, a stress marker index value, a physical fitness/integrity index, seizure data, seizure burden data and/or body data to determine a seizure severity index value (SSI value), as described above with respect to FIG. 1. In one embodiment, the SSI value may be indicative of the overall severity of a seizure event and/or extreme seizure event. The SSI value may also be indicative of the intensity, duration and/or spread of a seizure event. The SSI value may be transmitted/provided to seizure classification analysis unit 140, classification analysis comparator 142, responsive action unit 144, memory 117, monitoring unit 170, and/or remote device 192, among other units within the system comprising MD 100.

Figure 5B:
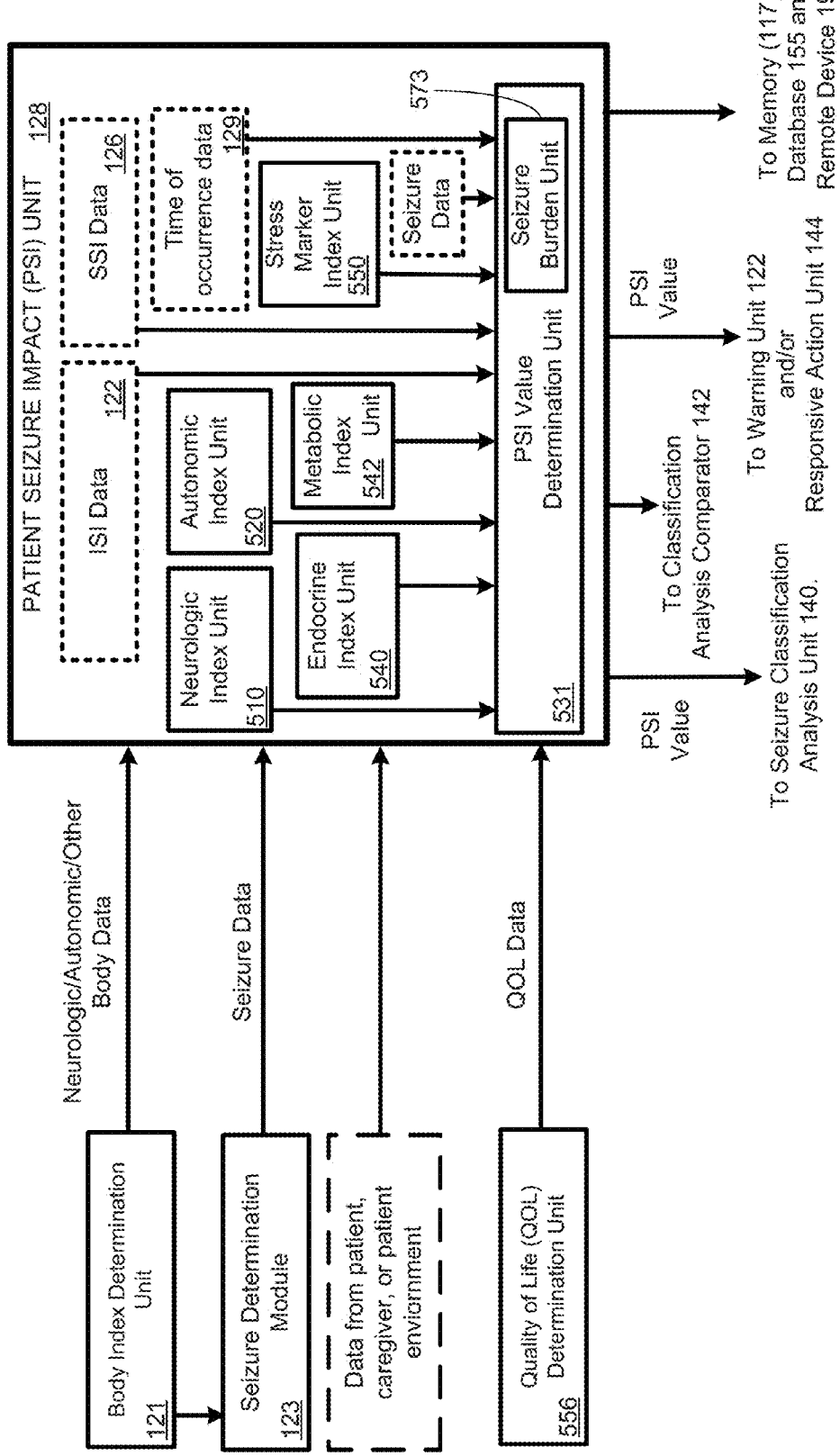
FIG. 5B provides a stylized diagram of a patient seizure impact unit for determining a patient impact using body data and/or seizure data, in accordance with one illustrative embodiment of the present invention.

Turning now to FIG. 5B, a block diagram depiction of a patient seizure impact unit (PIU) 128 is provided, in accordance with an illustrative embodiment. PIU 128 may be adapted to determine a patient seizure impact. ThePIU 128 may use body data (e.g., from data acquisition units 360, 370, 373, 374, 375, 376), seizure data from seizure determination unit 123, data input from a patient or caregiver, sensed information from the patient's environment, and/or stored data from memory 117. One or more subunits may be provided in PIU to determine different kinds of patient impacts associated with the seizure.

Data from various body index and/or data units may be provided to a Patient Seizure Impact value determination unit 531, which, together with information from seizure determination unit 123 and/or input data from the patient, a caregiver, or the patient's environment, is used to determine one or more patient seizure impact values. In one embodiment, data is provided to PSI value determination unit 531 from one or more of a sensor of the patient's environment, historical data from memory 117, a body index units such as neurologic index unit 510, autonomic index unit 520, endocrine index unit 540, metabolic index unit 542, tissue stress marker index unit 550, as well as seizure data (e.g., from seizure determination unit 123) and/or quality of life data from a quality of life determination unit 556.

Patient seizure impact value determination unit 531 may determine a number of different patient negative impacts, or identify conditions or activities that may increase the probability of a negative impact should the patient have a seizure while under those conditions or while performing those activities. Negative seizure impacts include but are not limited to periods of cardiac dysfunction (e.g., asystole or other arrhythmias that do not ordinarily accompany the patient's seizures or changes in the morphology of the P-QRS-T), changes in the normal respiratory rhythm (hyperventilationor apnea) or in the respiratory patterns (e.g., Cheyne-Stokes), extended periods of unresponsiveness beyond, e.g., the 90th percentile for the patient's historical seizures, cognitive deficits, depression, worsening of quality of life, deviations of metabolic or endocrine indices from normalcy, increase in the concentration or number of stress markers. In one embodiment, PIU 128 is capable of detecting one or more of a broken bone, head trauma and a brain contusion, caused by a fall caused by a seizure, burns, etc. In another embodiment, PIU 128 is capable of detecting the presence of risks in the patient's surrounding environment (e.g., taking a bath in a tub or walking downstairs), or of activities (e.g., swimming, operating power equipment) that may lead to injuries, even death, should the patient have a seizure while engaged in them. The PIU value may be transmitted/provided to one or more of seizure classification analysis unit 140, classification analysis comparator 142, responsive action unit 144, memory 117, monitoring unit 170, and/or remote device 192, among other units within the system comprising MD 100. PSI value determination unit 531 may further include a seizure burden unit 573, which may determine a seizure burden value for a patient based upon cumulative data determined by PSI value determination unit 531. Seizure burden unit may provide an indication of the overall burden of the patient's epilepsy to the patient's life as a result of PSI values determined over longer time periods such as weeks, months, or years.

Figure 5C:
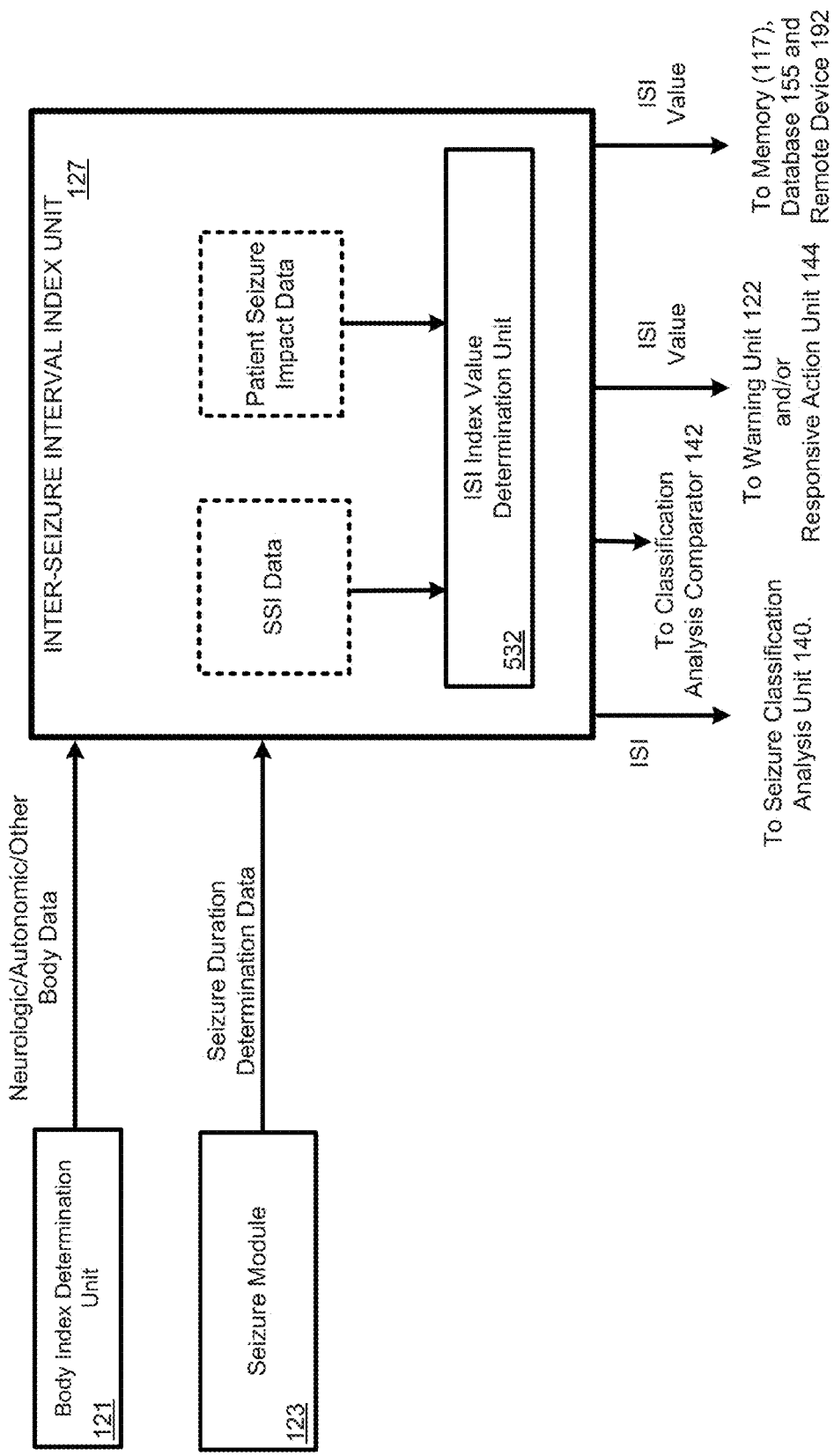
FIG. 5C provides a stylized diagram of an inter-seizure interval index unit for determining a time elapsed between seizures, or inter-seizure interval (ISI), using body data and/or seizure data, in accordance with one illustrative embodiment of the present invention.

Turning now to FIG. 5C, a block diagram depiction of an inter-seizure interval unit (ISIU) 127 is provided, in accordance with one illustrative embodiment. ISIU 127 may be adapted to determine an inter-seizure interval index (ISI index). The ISI unit 127 may use data from seizure determination unit 123 and/or Time of Occurrence Unit (TOU) 129, such as the time of detection of the seizure, the seizure end time, post-ictal start and end times, and similar data for prior seizures (e.g., from memory 117), seizure duration data, time spent in seizure data, seizure severity index data, patient seizure impact data, time of occurrence data, and other data in determining the ISI index. In one embodiment, body data may include, but is not limited to, neurologic and/or autonomic body data, endocrine data, stress marker data, physical activity data, and/or the like. Various data described above, alone or in any combination may be transmitted to an ISI index value determination unit 532. The ISI index value determination unit 532 may use a neurologic index value, an autonomic index value, an endocrine index value, a stress marker index value, a physical fitness index seizure data, and/or other body data to determine an inter-seizure interval index value (ISI index value), as described above with respect to FIG. 1.

In one embodiment, the ISI index value may be indicative of the overall severity of one or more seizure events and/or extreme seizure events based upon one or more intervals of time between events. Decreasing or shortened intervals (compared to reference values) between successive seizures may indicate a medical emergency for the patient (e.g., status epilepticus and/or an elevated risk of Sudden Death in Epilepsy, or SUDEP). The ISI index value may also be indicative of the intensity, duration and/or spread of one or more seizure/extreme seizure events had by a patient. The ISI index value may be transmitted/provided to one or more of seizure classification analysis unit 140, classification analysis comparator 142, responsive action unit 144, memory 117, monitoring unit 170, and/or remote device 192, among other units within the system comprising MD 100.

Figure 5D:
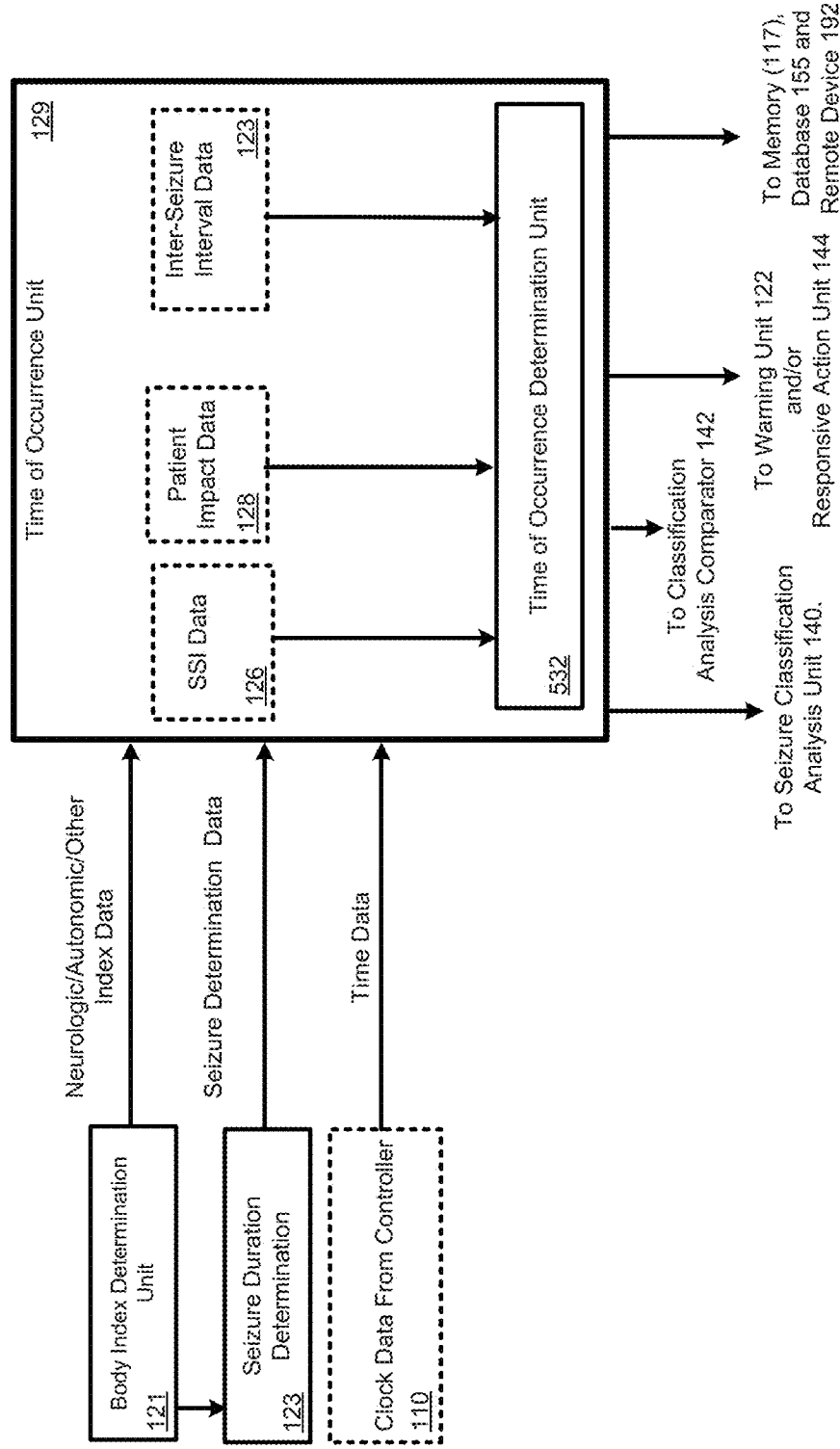
FIG. 5D provides a stylized diagram of a Time of Occurrence Unit for determining a time of occurrence of a seizure, in accordance with one illustrative embodiment of the present invention.

FIG. 5D provides a block diagram depiction of a Time of Occurrence Unit (TOU) 129, in accordance with one illustrative embodiment. TOU 129 may be adapted to determine a time of occurrence of a seizure. This may in one embodiment constitute determining and logging a simple timestamp for transmission to a monitoring unit, which then determines, e.g., the date & year, and time of day at which a seizure event occurs. In other embodiments, the MD 100 itself determines the date, year and time of day of the seizure event. In addition, the TOU 129 may also provide time information related to the seizure based upon body data, such as the end time of the seizure, the time from detection to one or more other occurrences, such as one or more body indices reaching a particular value (e.g., the time between seizure onset and maximum heart rate, the time between seizure onset and the patient becoming unresponsive, or other events that may provide meaningful information of the seizure by relating it to time of seizure onset).

TOU 129 may use data from body index determination unit 121, a clock (e.g., a clock in controller 110), seizure determination unit 123, SSI, ISI, or patient seizure impact (PSI) data, and/or one or more of body index determination units 510, 520, 540, 542, 550, etc.). Various data described above, alone or in any combination may be transmitted to a time of occurrence determination unit 533. The TOU determination unit 533 may use the foregoing data to determine a time of occurrence value described above. Time of occurrence values may be transmitted/provided to one or more of classification analysis unit 140, classification analysis comparator 142, responsive action unit 144, memory 117, monitoring unit 170, and/or remote device 192, among other units within the system comprising MD 100.

Figure 6:
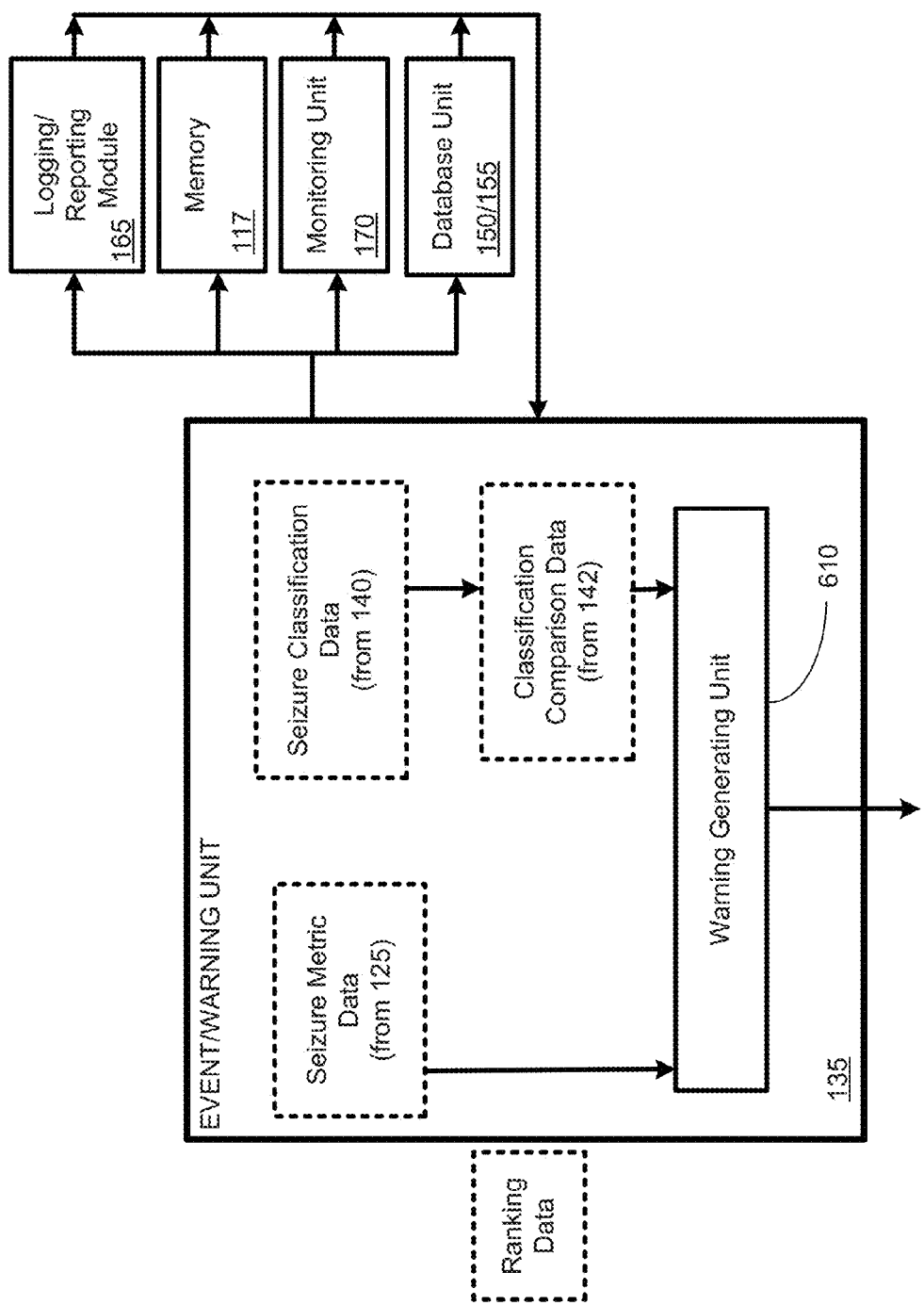
FIG. 6 provides a stylized diagram of an event/warning unit for warning of, and/or taking other action in response to a patient's seizure, in accordance with one illustrative embodiment of the present invention.

Turning now to FIG. 6, a block diagram depiction of an event/warning unit 135 is provided, in accordance with one illustrative embodiment of the present invention. In one embodiment, the event/warning unit 135 may be adapted to provide a warning of a seizure event, a seizure classification, and/or a result of a comparison of two or more seizure classification analyses. In various embodiments, seizure events and/or extreme seizure events may include a seizure, a severe seizure, a present or past state of status epilepticus, an increased risk of a state of status epilepticus, a risk of SUDEP, a result of a seizure classification analysis, a feature of a seizure class, a result of a comparison of a seizure classification analyses, a change in a seizure class, or the emergence of a new seizure class or the disappearance of a seizure class. The event/warning unit 135 may provide a warning to a patient, a physician, a care giver, the logging/reporting module 165, the monitoring unitl 70, the remote device 192, the memory 117, the database 150/1255, and/or the like.

The event/warning unit 135 may include a warning generating unit 610, in accordance with one embodiment. The event/warning unit 135 may be adapted to receive extreme epileptic event/state data from extreme epileptic event/state detection, seizure metric data from SMDU 125, seizure class information from seizure classification analysis unit 140, and changes in seizure classes from classification analysis comparator 142. In various embodiments, the event/warning unit 135 may be adapted to receive other signals and/or data in addition to, or alternatively to, the aforementioned data, as shown in FIG. 6. In one embodiment, the warning generating unit 610 may take any data received by the event/warning unit 135 as an input to generate a warning. The warning may be a general warning related to a seizure or seizure event, and/or an indication or warning of status epilepticus. In one embodiment, the event/warning unit 135 may include a warning regarding a seizure class or a change in a seizure class from seizure classification analysis unit 140 and/or classification analysis comparator 142.

The warning may manifest as a warning tone or light implemented by a nearby object adapted to receive the indication of a seizure event from the MD 100; an automated email, text message, telephone call, or video message sent from the MD 100, either directly or via an monitoring unit 170, to an emergency dispatch system, the patient's cellular telephone, PDA, computer, etc. The characteristics of the warning may depend on the type and severity of an event or of the detected change. The warning may include a time indication (e.g., date and time) of when the warning was issued, to enable a patient or caregiver to appreciate that the patient's condition may be deteriorating, improving, or stable and the correlations, if any, with circadian or other biological rhythms (e.g., menses). Warning indications may be logged and significant changes in severity, type, frequency, or intervals of warnings may, in some embodiments, be used to provide further warnings or alerts. Such a warning may allow the patient or his/her physician/caregivers to take measures protective of the patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc.

Figure 7:
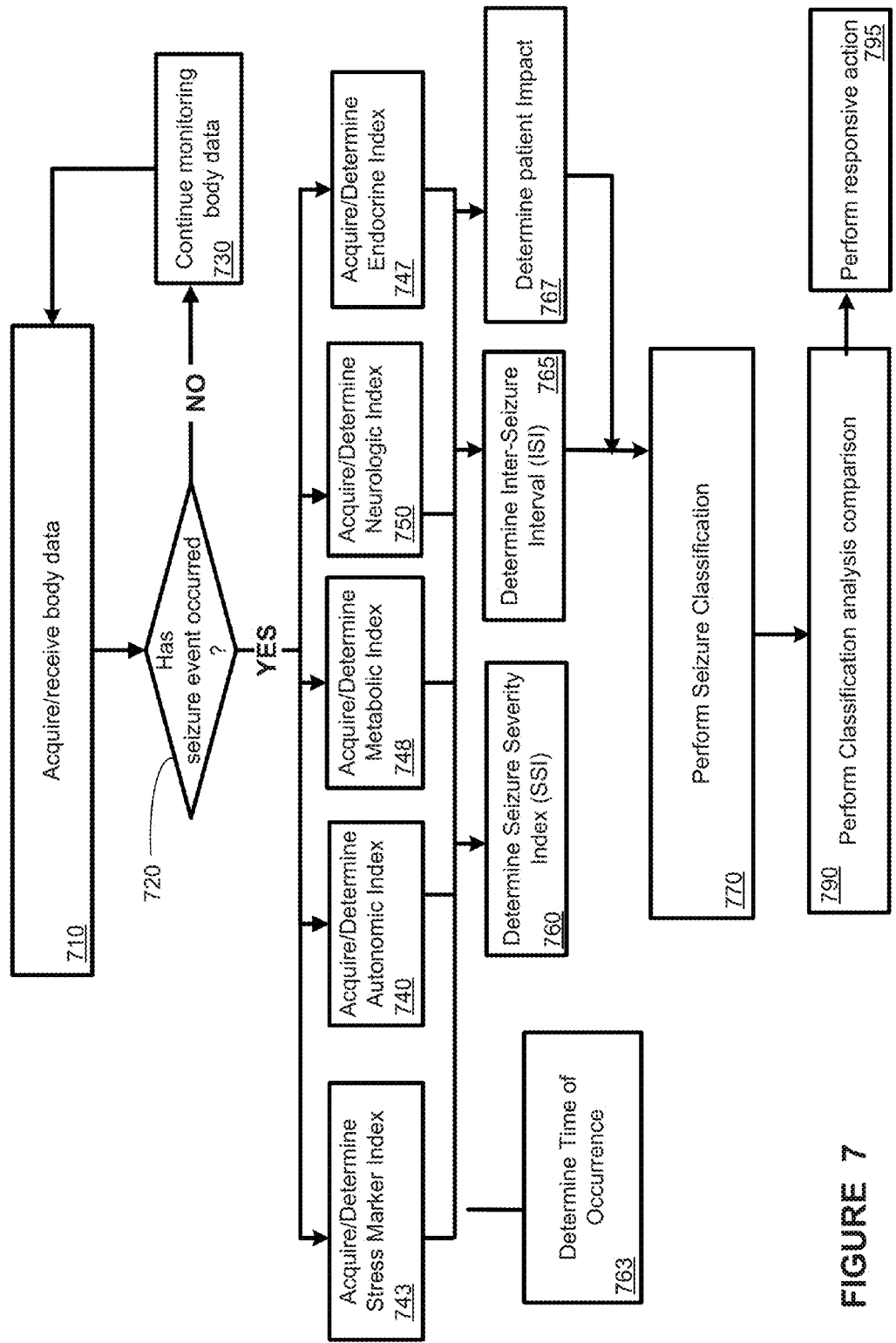
FIG. 7 provides a flowchart depiction of a method for classifying seizure events, in accordance with one illustrative embodiment of the present invention.

Turning now to FIG. 7, a flowchart depiction of a method for determining seizure metrics, performing seizure classification(s), performing classification comparison, and/or taking action in response to a classification or classification comparison is provided, in accordance with one illustrative embodiment of the present invention. The MD 100 acquires and/or receives body data (step 710). The data may be provided by one or more body data acquisition units such as units 360-370 and 373-377 (see FIGS. 3, 4), which may include, e.g., electrodes, accelerometers, chemical sensors, thermal sensors, pressure sensors, optical sensors and other structures to sense body signals of the patient. In one embodiment, the body index determination unit 121 receives the body data, which may be indicative of whether or not a seizure or seizure event has occurred or is likely to occur. After performing buffering, amplification, and A/D conversion of the body data, body index determination unit may determine one or more body indices derived from the data.

The body index/indices determined by BIDU 121 may be stored, e.g., in memory 117 and/or provided to seizure determination unit 123, which may use one or more algorithms to process the body index/indices determined by BIDU 121 to determine whether or not a seizure event has occurred (720). In some embodiments, all or portions of the body index determination function or unit 121 may be provided as part of seizure determination unit 123. Details on using multiple streams of body data to detect seizures are provided in co-pending United States application Ser. No. 12/896,525 filed Oct. 1, 2010, Ser. No. 13/098,262 filed Apr. 29, 2011, and Ser. No. 13/288,886 filed Nov. 3, 2011, each incorporated by reference herein. If the MD 100 determines that no seizure or seizure event has occurred, the MD 100 will continue to monitor for body data (step 730) and return to step 710.

MD 100 may use one or more body indices determined by BIDU 121 to detect the occurrence of a seizure event. If MD 100 determines (step 720) that a seizure event has occurred or is likely to occur, the method proceeds to determine or acquire an autonomic index (step 740), a neurologic index (step 750), a tissue stress marker index (step 743), a metabolic index (step 748) and/or an endocrine index (step 747). In one embodiment, the autonomic index, the neurologic index, the stress marker index, the metabolic index and/or the endocrine index/indices are acquired and/or determined using an SSI unit 126 (typically comprising an autonomic index unit 520, a neurologic index unit 510, an endocrine index unit 540, metabolic index unit 542 and/or a stress marker index unit 550). Steps 740, 743, 747-748 and/or 750 may begin at the same time and end at the same time, or at different times, according to different embodiments contemplated herein. In other words, steps 740, 743, 747-748 and/or 750 may begin and be completed substantially in parallel (i.e., at approximately the same time or at the same time), in series, or independently of each other.

The medical device may determine one or more seizure metrics using seizure metric determination unit (SMDU) 125. Seizure metrics may include using the autonomic index, the neurologic index, the stress marker index, the metabolic index and/or the endocrine index to determine an SSI value (step 760); an inter-seizure interval index (ISI index) value (step 765); a patient impact (PI) value (step 767). Other seizure metrics may include a time of occurrence of the seizure event (step 763). Typically, the SSI value is determined by SSI unit 126 (which may comprise an SSI determination unit (530)). In one or more embodiments, additional data may also be used to determine the SSI value. Typically, the ISI index value is determined by ISI unit 127. In one or more embodiments, additional data may also be used to determine the ISI index value. The determination of the SSI value and the ISI index value may occur in parallel or at different times. In one embodiment, only one of the values may be determined. For example, in one embodiment, only the SSI value may be calculated while no ISI index value is calculated. In another embodiment, only the ISI index value may be calculated while no SSI value is calculated.

Once one or more of an SSI value (step 760), an ISI value (step 765), a PI value (step 761, and/or a time of occurrence (step 763) is determined, MD 100 may perform one or more seizure classification analyses (step 770) to determine one or more seizure classes based on the seizure metric values determined in steps 760-765. The seizure classification analysis may be performed by SCA unit 140 (FIG. 1). After the seizure classification analysis, the method may proceed to comparing one or more classification analyses (step 790) to identify changes in one or more seizure classes. The comparison of the classification analyses may be performed by the classification analysis comparator 142 (FIG. 1). The MD 100 may then take responsive action(s) based upon the seizure classification and/or the classification analysis comparison. Responsive actions may include providing a warning, providing a therapy (e.g., drug/chemical therapy, electric stimulation, cooling, supportive care, oxygen administration), logging/reporting, and/or the like.

Figure 8:
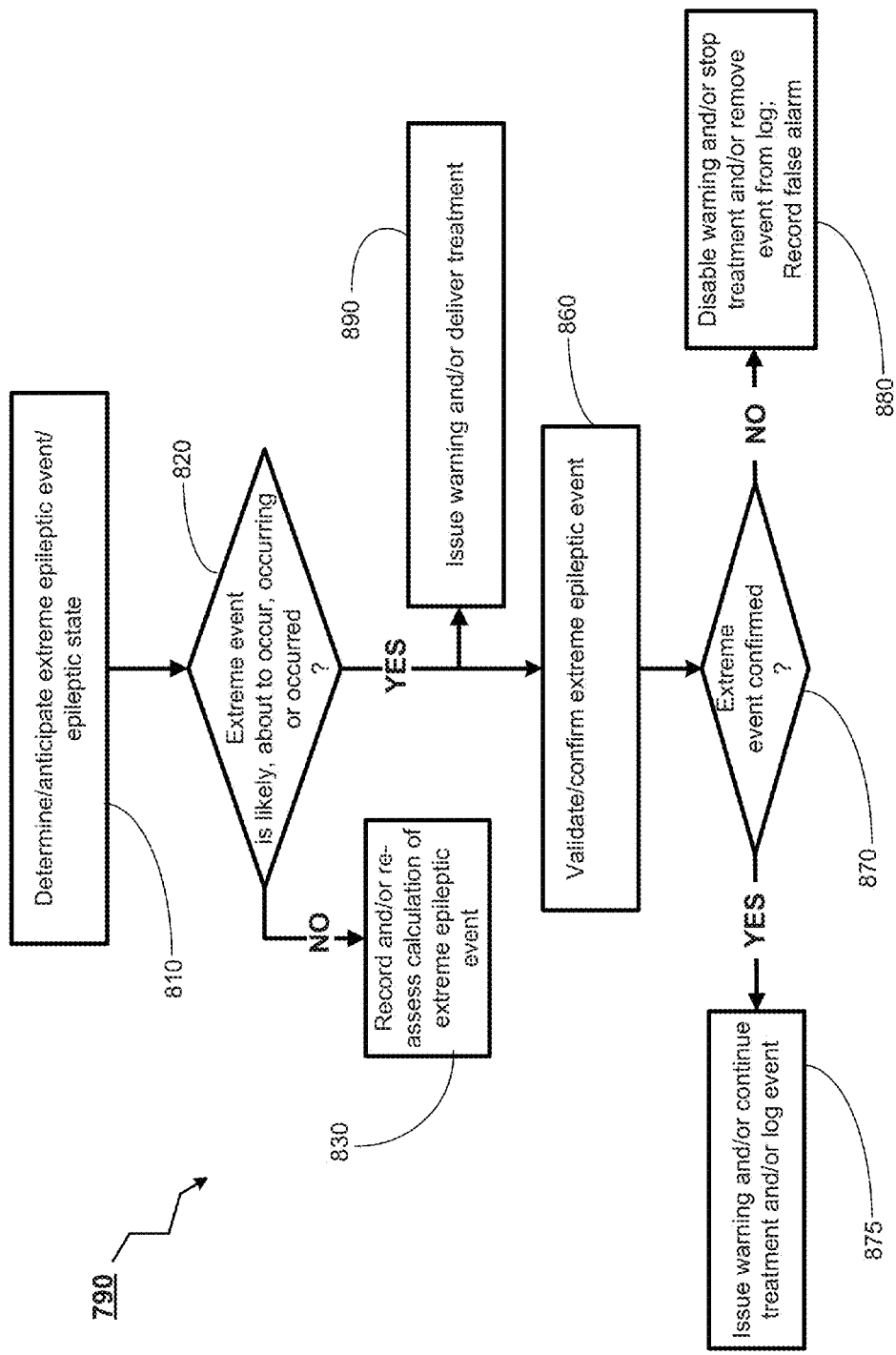
FIG. 8 provides a flowchart depiction of a method for implementing responsive actions (warning, treatment, or data logging, among others) in response to determining that extreme events are probable, are occurring, or have occurred, in accordance with one illustrative embodiment of the present invention.

FIG. 8 is a flowchart depicting a method for warning and/or taking action in response to determining an extreme seizure event. FIG. 8 is substantially similar to FIG. 8 of co-pending U.S. application Ser. No. 13/040,996. A discussion of FIG. 8 herein is provided in the '996 application.

Figure 9:
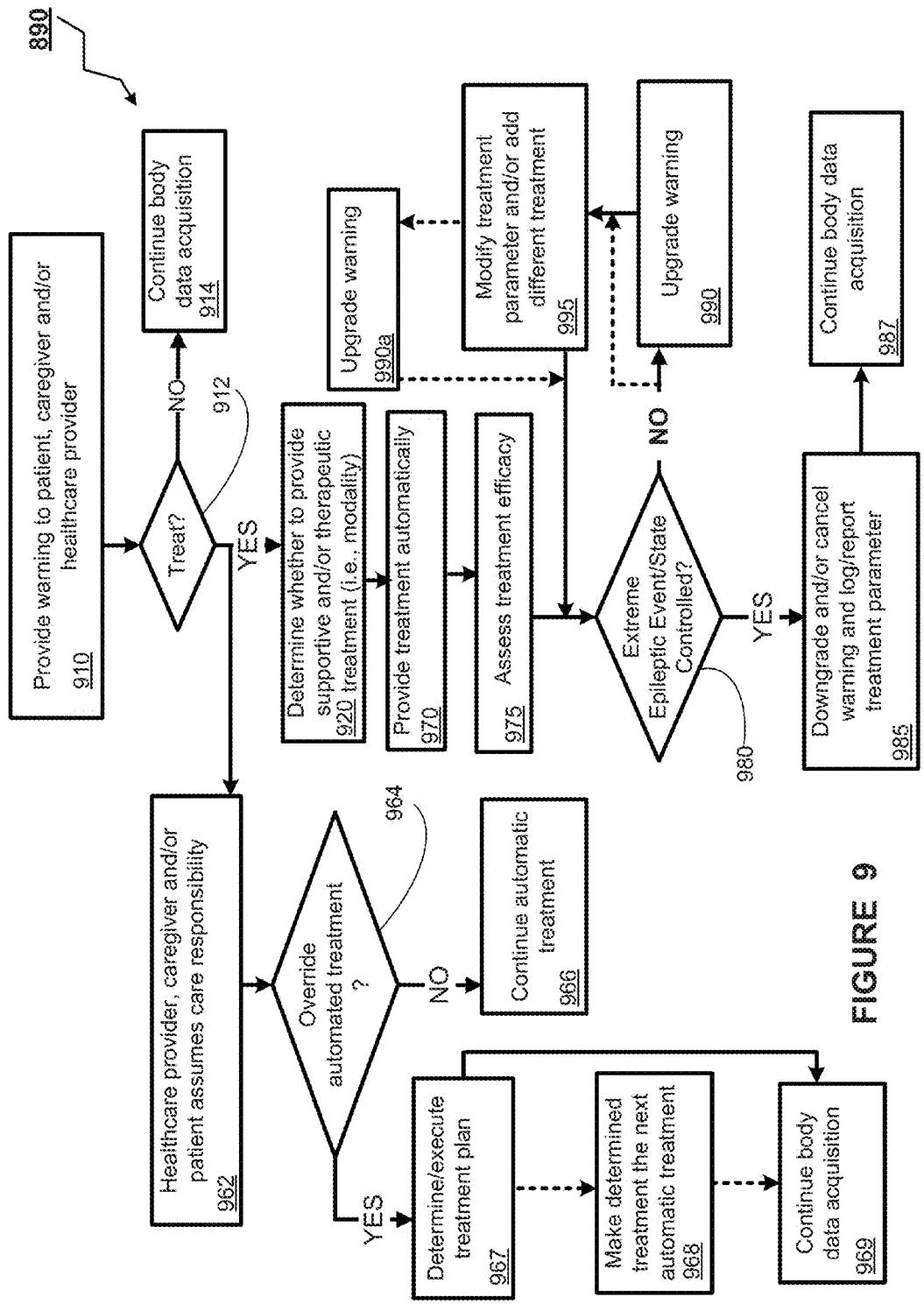
FIG. 9 provides a flowchart depiction of a method for warning and/or providing a treatment to a patient likely to be in or recently have been in an extreme epileptic event, in accordance with one illustrative embodiment of the present invention.
Figure 10:
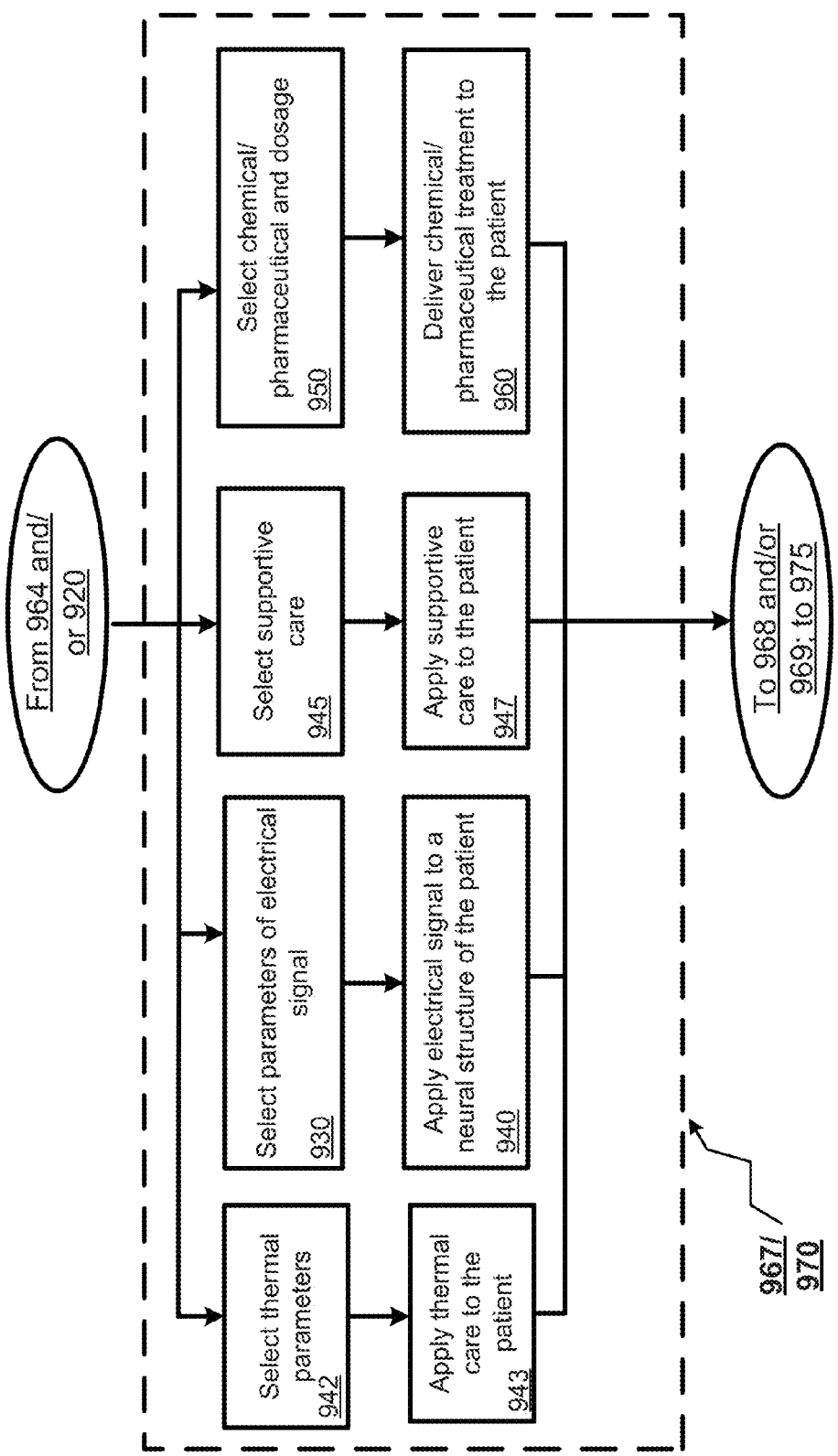
FIG. 10 illustrates a stylized diagram of determining and executing a treatment plan by a healthcare provider, caregiver, and/or patient subsequent to overriding automated treatment, in accordance with one illustrative embodiment of the present invention.

FIG. 9 provides a flowchart depicting a method for warning and/or providing a treatment to a patient in response to a seizure event and/or extreme seizure event, and FIG. 10 is a stylized depiction of the step of determining a non-automatic treatment plan of steps 967/970 of FIG. 9. FIGS. 9 and 10 are substantially similar to FIGS. 9 and 10 of co-pending U.S. application Ser. No. 13/040,996. A discussion of FIGS. 9 and 10 herein is provided in the '996 application.

Figure 11:
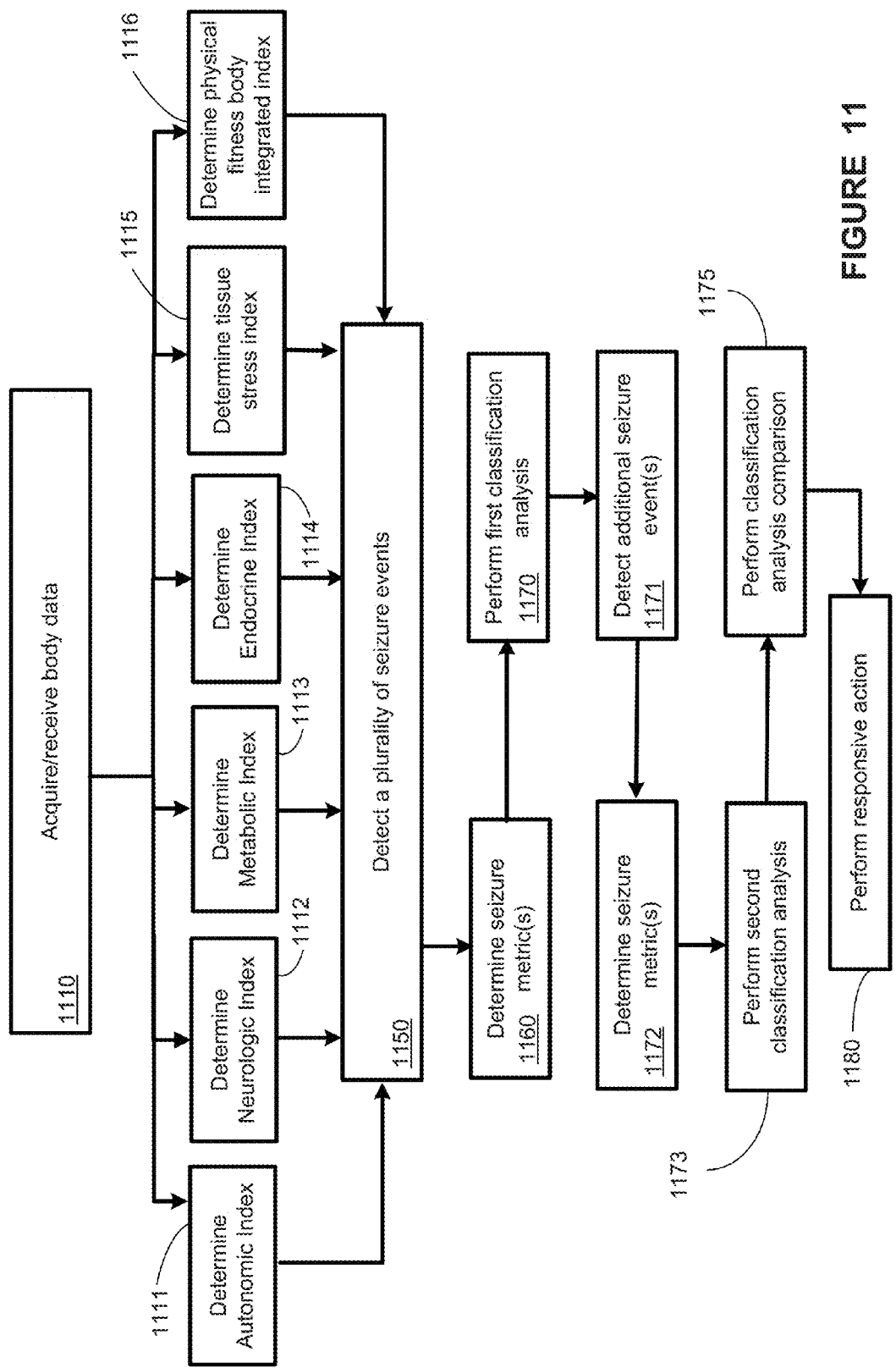
FIG. 11 provides a flowchart depiction of a method for identifying and/or managing a seizure event, in accordance with one illustrative embodiment of the present invention.

Turning now to FIG. 11, a flowchart depiction of a method for identifying changes in an epilepsy patient's disease state or condition by performing classification analyses is provided, in accordance with one illustrative embodiment of the invention. The medical device 100 acquires and/or receives body data at step 1110, typically by body index determination unit 121. The body data may be indicative of whether or not a seizure or seizure event has occurred, is occurring or is likely to occur. After performing buffering, amplification and A/D conversion of the body data, the MD 100 determines at least one body index (1111-16). Body index determination unit 121 may determine one or more body indices for detection of seizure events. The indices may be one or more of an autonomic index (1111), a neurologic index (1112), a metabolic index (1113), an endocrine index (1114), a tissue index or a tissue stress index (1115), a physical fitness index/body integrity index (1116), or a quality of life index (not shown).

The one or more indices may be used to detect a plurality of seizure events (1150). In one embodiment, seizures in the plurality of seizure events may be detected by the seizure determination unit 123 using different body indices. For example, a first seizure event may be detected by using an autonomic index such as heart rate, while a second seizure event may be detected by a body kinetic/accelerometer signal. If the medical device 100 determines that no seizure or seizure event has occurred, the medical device 100 will continue to monitor for body data until a seizure event is detected.

The MD 100 determines at least one seizure metric for each seizure of the plurality of detected seizure events (1160). In one embodiment, seizure metric determination unit (SDMU) 125 determines one or more seizure metric values for each seizure event. Seizure metrics may include seizure severity indices determined by SSIU 126, inter-seizure intervals determined by ISIU 127, patient seizure impact values determined by PIU 128, and times of occurrence determined by TOU 129 (see FIG. 1). In some embodiments, seizure metrics are determined for each seizure substantially at the time the seizure is detected. In other embodiments, seizure metric values may be determined after detection of a plurality of seizure events. Seizure metric values may in some embodiments be normalized or adjusted based on circadian fluctuations and other patient or environmental factors.

Returning to FIG. 11, after seizure metrics are determined for a plurality of seizure events, the method also includes performing a first classification analysis on the plurality of seizures (1170). The first classification analysis may include identifying one or more classes of seizures. As previously noted, the classification analysis may involve creating an n-dimensional phase space to classify seizure events. The phase space may consist of n seizure metrics, and the n seizure metrics may be selected form a larger m-dimensional matrix of indices that is maintained for each seizure event.

The method also comprises detecting additional seizure events (1171). This may be accomplished by seizure determination unit 123. The additional seizures may be determined in some embodiments using data from body index determination unit 121. Seizure metrics for the additional seizure events are determined (1172) by SMDU 125 (e.g., by one or more of SSIU 126, ISIU 127, PIU 128, and TOU 129).

A second classification analysis is performed (step 1173). This may be done by seizure classification analysis unit 140 in some embodiments, while separate classification analysis units may be used for each of the first and second classification analyses in different embodiments. In one embodiment, the second classification is made on both the plurality of seizure events analyzed in the first seizure analysis plus the additional seizure events. In other embodiments, the second classification may include some, but not all, of the plurality of seizure events in the first classification analysis as well as the additional seizure events. In still further embodiments, the second classification is made only on the additional seizure events.

A comparison of the first and second classification analyses is performed (1175). In some embodiments, the comparison of the first and second seizure analyses may yield information regarding changes in one or more seizure classes from the first to the second classification analysis, the emergence of new classes, or seizures that do not fit within any existing classes.

The comparison of the first and second analyses may be used to initiate one or more responsive actions (1180). Illustrative responsive actions may include reporting a change from the first classification to the second classification (e.g., a seizure class identified in the first classification analysis is growing, shrinking, increasing in density, changing shape, shifting its centroid, etc.); reporting the absence of a change from the first classification to the second classification (e.g., a seizure class identified in the first classification has not changed); displaying a result of at least one of the first classification analysis, the second classification analysis, and the comparison; identifying the emergence of a new class in the second classification analysis that was not present in the first classification analysis; identifying the disappearance of a class in the second classification analysis that was present in the first classification analysis; identifying one or more seizure events that are not part of any class; providing a therapy to a patient; identifying an effect of a therapy; identifying a proposed change in therapy; identifying a proposed additional therapy; and identifying an extreme seizure event. Any changes in seizure classifications may then be reported, in one embodiment, as either deterioration (e.g., appearance of a class of severe seizures that has increased the disease burden); improvement (e.g., disappearance of a class of severe seizures with consequent lessening in the disease burden) or stable disease (e.g., no changes in classification). Other or additional responsive actions—such as warnings if the disease burden is increasing—may be implemented in response to a classification analysis or a comparison of classification analyses. In one embodiment, a seizure metric includes whether the seizure detection was followed by a responsive action to provide a therapy to the patient. In such embodiments, the classification analysis may include whether the seizure was treated or not, and the effect of the treatment efficacious, no effects, adverse effects). In a particular embodiment the classification analysis comparison may include comparing treated and untreated seizures. This may facilitate identification of efficacious or undesirable seizure treatments, including treatments that are effective or undesirable for particular classes of seizure events.

The seizure classification analyses performed in methods according to FIG. 11 may be performed in a variety of different mathematical and graphical ways. In one embodiment, a classification analysis refers to a qualitative, semi-quantitative, or quantitative analysis of one or more seizure metric values (e.g., SSI values as a function of time with respect to a threshold) or a statistical analysis (e.g., a histogram) with respect to a number of standard deviations away from an actual or realized "normal" distribution. Seizures may be classified into one or more groups according to seizure metric values such as one or more seizure severity indices (e.g., seizure duration, maximum heart rate, heart rate increase from a reference heart rate, etc.), inter-seizure intervals between a seizure and one or more other seizures, the impact on a patient and/or other bases relevant for classifying seizures (e.g., type of seizure).

The seizure classification obtainable through this disclosure, may expand the known classes (e.g., generalized vs. partial and for partial, simple vs. complex), to include other measurable aspects of seizures in a quantitative manner. For example, in the case of a patient with seizures characterized by:
a) an unprovoked expression of fear for 10 sec. without increase motor activity but with tachycardia (peak heart rate: 135 beats/min with reference/non-seizure mean heart rate of 82);
b) reversible 2 mm. S-T depression (reference EKG: normal);
c) blood pressure (BP) elevation (BP of 138/89 vs. reference non-seizure BP of 112/70);
d) hyperventilation (peak respiratory rate: 21 breaths/min with reference/non-seizure mean respiratory rate of 10 breaths/min.);
e) loss of awareness as ascertained using a complex reaction time test, (patient failed test 28 sec after first seizure manifestation (no failure during non-seizure state) and awareness remained impaired compared to reference/non-seizure reaction time values for 45 min after termination abnormal electrical activity);
f) motionless late in the course of the seizure (accelerometer register no motion in the standing position for 65 sec compared to 10 sec for reference/non-seizure upright posture);
g) arterial respiratory alkalosis (pH 7.5 vs. mean reference pH of 7.38) and prolactin elevation (30 µg/L with mean reference level of 15 µg/L),
this seizure will be classified as partial complex with emotional (fear for 10 sec), neurologic (loss of awareness for 45 min), hypomotoric (for 65 sec), cardiac (43 beat/min increase in rate and ST depression of 2 mm), hyperventilation (11 breaths/min increase in rate), arterial alkalosis (pH elevated by 0.5) and endocrine (prolactin elevation of 15 µg/L) manifestations. The duration (in sec., min., or hours) of these changes may be included in the quantification/classification for added detail. The spread of this seizure (which was not treated) may be tracked using the temporal evolution of changes in the various indices. The reaction time test failure (28 sec after the first clinical manifestation) and motionlessness are indications that the seizure spread from its emergence network (as amygdala and hippocampus) to other networks such as the contra-lateral hippocampal formation. An unprovoked expression of fear and tachycardia in this patient may automatically trigger delivery of therapy to either: the commissures (anterior and/or psalterium) connecting the two mesial temporal networks and/or to the unaffected mesial temporal network to prevent invasion by abnormal activity.

Classification analyses may be based upon a graphical analysis of, e.g., an SSI value versus time, or a first SSI value versus a second SSI value. More generally, a classification analysis may be performed using any one or more elements of a matrix to create an n-dimensional classification space, within which the seizure events may be located. Results of the classification analysis may be displayed to a user, or used as a basis for taking one or more additional actions such as providing a warning to a user or caregiver, or providing or modifying a therapy.

For example, in one illustrative embodiment, a patient may have a first classification group of seizure events having a relatively short duration and a relatively low intensity, and a second, smaller classification group of seizure events having a relatively long duration and a relatively high intensity. Classes and subclasses may be identified depending upon the closeness or proximity among the metrics of seizure events. If a seizure event classification group (which may also be referred to as a seizure class) changes as additional seizures occur (e.g., the class grows due to increases in average duration and/or average intensity of newly detected seizures or a new class emerges as dictated by the severity of newly detected seizures), this may indicate worsening of the patient's epilepsy along with, for example, increased risk of status epilepticus, seizure burden, or sudden death. Similarly, if a seizure class shifts its position, (e.g., inwardly and towards the origin on a plot of seizure duration versus intensity) causing the distance (graphically) between two seizure classes to decrease, such a shift/increase may represent an improvement in the patient's epilepsy along, for example, with a decreased risk of status epilepticus or SUDEP. In an alternate embodiment, the SSI value(s) may be determined by normalizing a seizure intensity value, a seizure duration value and/or a seizure spread value (or a seizure severity value) to obtain respective percentile values. The percentile values may then be averaged to determine a composite, normalized SSI for a plurality of seizures.

Seizure classification analyses performed by seizure classification analysis unit 140 may involve supervised learning algorithms in some embodiments and unsupervised learning algorithms in other embodiments. Embodiments involving supervised learning include pattern matching (such as a matched filter to which a seizure index pattern is compared) or many varieties of pattern recognition techniques. Techniques of pattern recognition include using an n-dimension vector of features to identify classes; a dot-product or angular filter, identifying categorical (e.g., extreme) or ordinal (e.g., integer-valued or real-valued) classes. Pattern recognition techniques may be probabilistic or deterministic. Probabilistic techniques may include, e.g., a maximum entropy classifier, a naïve Bayesian classifier, a support vector machine (SVM), kernel estimation and k-nearest neighbor techniques; decision trees.

In some embodiments, classification analyses may involve clustering algorithms. Exemplary clustering algorithms may include categorical mixture models, K-means clustering, hierarchical clustering (including agglomerative and divisive methods), kernel principal component analyses, regression algorithms. Clustering techniques may be supervised, such as linear regression extensions and artificial neural analysis, and Gaussian process regression, or unsupervised. Cluster models include connectivity or distance-based models focusing on the distances between seizures in an n-dimensional phase space, and centroid-based models (K-means models) in which seizure clusters can be represented as a single median vector of all seizure events. Other clustering techniques include distribution models (e.g., statistical distributions such a multivariate distributions normalized by expectation maximizing algorithms), density models (e.g., identifying dense regions in a phase space), and subspace models (e.g., bi-clustering and co-clustering techniques) are other clustering techniques that may be applied to seizure classification in view of the disclosures herein.

Other techniques include categorical sequence labeling algorithms, both supervised and unsupervised, including hidden Markov modeling (HMM), maximum entropy Markov modeling, and conditional Ransom fields.

In some embodiments, real-valued sequence labeling algorithms may be used to classify seizures based on seizure metrics. These algorithms may include the use of Kalman filters and particle filters. Parsing algorithms, also referred to as predictive tree-structure labels, may be used and may be supervised or unsupervised. One such technique involves probabilistic context-free grammar.

In some embodiments, so-called ensemble algorithms may be employed. In one embodiment, ensemble algorithms may involve supervised meta-algorithms for combining multiple learning algorithms together to classify seizures based on seizure metric data compiled for a plurality of seizure events. Ensemble algorithms may include bootstrap aggregating techniques, boosting techniques, ensemble averaging, mixture-of-experts, and hierarchical mixture-of-experts.

Results of classification analyses may be displayed for a user in a variety of ways. In one embodiment, a seizure classification may involve displaying a plurality of seizures graphically using a SSI metric (Y-axis) and time of occurrence (X-axis). Clustering techniques as described above may be used to identify seizure classes, such as identifying recent, severe seizures or, mild seizures. The SSI metric may be used to identify a variety of severity-based classes, such as seizures below mean SSI values, within a specified SSI range, elevated, and critically elevated. Time of occurrence (e.g., time of day, seizures occurring within the past 1 week, past 1 month, past 1 year, etc.), may be used to select seizures for classification purposes.

Figure 12:
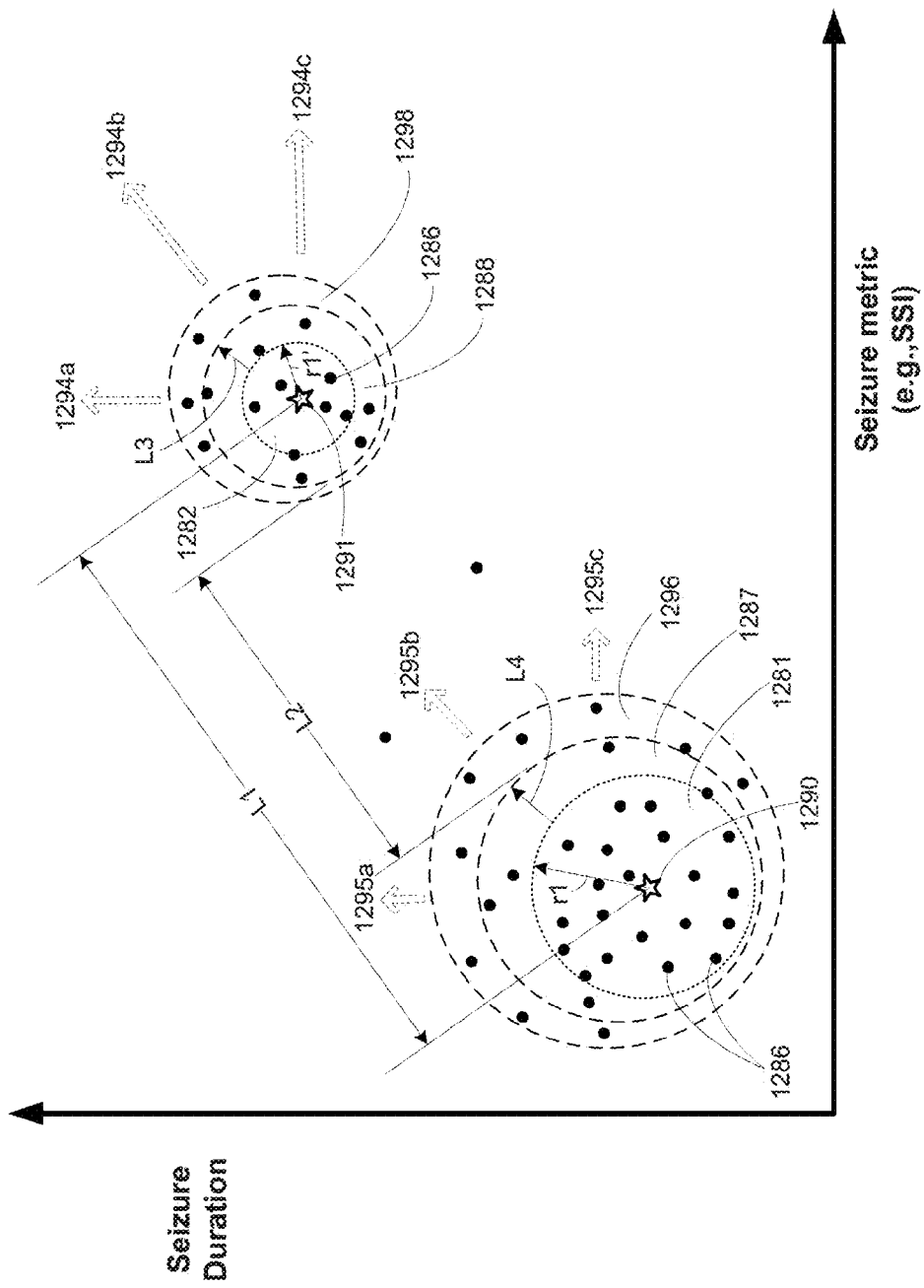
FIG. 12 provides a stylized depiction of a graph relating to an exemplary seizure classification analysis, in accordance with one illustrative embodiment of the present invention.

Turning now to FIG. 12, a stylized depiction of a graph indicative of the results of an exemplary classification analysis is provided in accordance with one or more embodiments. In the illustrated embodiment, the y-axis depicts a seizure metric, in this instance seizure duration and the x-axis depicts a seizure metric (e.g., an intensity measure such as an SSI). Other indices (or more generally, one or more elements in an n-dimensional seizure index matrix) could be used to perform either several univariate or multi-variate classification analyses in accordance with various embodiments, by selecting for example the time of day a seizure occurs, the maximum acceleration recorded by an accelerometer during the seizure, the time from seizure onset until a fall occurs during a seizure, a patient impact (PI) index of a seizure, an inter-seizure interval (ISI), a SSI disclosed herein, or any other seizure variables. For example, in one embodiment a microphone may be used to record the duration, frequency spectrum and decibel level of sounds such as the so-called "epileptic cry" associated with a seizure, and track this variable over time to identify changes, if any, in said seizures and in the class to which they have been assigned. In another embodiment, devices to measure noise (in db) or luminance (in candles or lumens) may be used to determine whether a seizure was precipitated by certain frequency type/level of noise or by certain wavelength(s) of light or electromagnetic radiation, for the purpose of instituting preventive steps and/or treatment. Many other quantities may be used in graphs of the type disclosed generally in FIG. 12, and remain within the spirit and scope of the present invention.

The classification analysis in FIG. 12 is a two-dimensional illustration of two seizure classes 1281 and 1282 of seizure events 1286 (seizures are represented by dots). A comparison of the two seizure classes may result in one or more measures characterizing the seizures classes, and/or differences between the two seizure classes. For example, in FIG. 12, seizure classes 1281 and 1282 may, as additional seizures occur, change to classes 1287 and 1288, respectively. This change indicates that classes 1281 and 1282 both are enlarging, changing shape, or migrating in becoming seizure classes 1287 and 1288 respectively. The change in class size (e.g., area or volume, or multidimensional capacity) may, in some cases, be indicative of the region in the analysis in which the seizure events 1285 are distributed.

In one embodiment, the measures (e.g., one or more indices) characterizing each seizure class may in turn be used to define a phase space, or a seizure class space. In another embodiment, the measures or metrics used to define a seizure class may be used to compare it to other classes, and to determine one or more differences between the classes. For example, in FIG. 12, seizure classes 1281 and 1282 may be separated by a distance L1 (i.e., a distance between the centroids 1290 and 1291 respectively, of seizure classes 1281 and 1282). Distance L1 may be measured using Euclidian methods (for example, from the centroid 1290 of seizure class 1281 to the centroid 1291 of seizure class 1282) or non-Euclidian methods. In alternative embodiments, the distance L1 may be measured using different points (i.e., measures other than the centroid that characterize the seizure class as a whole) of seizure classes 1281 and 1282. For example, another measure of the differences between seizure classes 1281 and 1282 may be indicated by a distance (not shown) measured by the closest two points of the respective class boundaries), measured using Euclidian and/or non-Euclidian methods.

In one or more embodiments, changes to one or more seizure classes over time (i.e., as additional seizure events occur and are classified) may indicate that a patient has a risk/increased risk of an extreme seizure event/state, or that the patient is having an extreme seizure event. For example, an increase in the distance L1 due to an outward shift of the boundary of seizure class 1282 (via any of the arrows 1294 ($a$-$c$)) may indicate that seizure class 1282 is becoming more severe overall and thus that the patient's epilepsy is more severe and there is a deterioration in the patient's condition, or that the patient is in an extreme seizure state. Similarly, an outward shift of the boundary of seizure class 1281 (via any of the arrows 1295($a$-$c$)) may indicate that seizure class 1281 is becoming more severe overall and thus that the patient's condition is deteriorating, or that the patient is in an extreme seizure state. This may be the case even though an outward shift in the boundary of seizure class 1281 (via any of the arrows 1295($a$-$c$)) may actually reduce the distance L1 between seizure class 1281 and seizure class 1282. In an alternative embodiment, an increased/increasing risk of an extreme seizure event/state may exist even though a decrease in overall distance between the seizure classes occurs. In such a case, the relative distance of seizure classes 1281 and 1282 may be measured to determine a risk/increased risk of an extreme seizure event/state, or that the patient is in an extreme seizure state by the following formula:

$$L1 = r1 + r1' + L2,$$

where r1 is the radius of seizure class 1281 and r1' is the radius of seizure class 1282.

Under this formula, if L decreases because of seizure class translation (as shown, e.g., by a shift towards the graph's origin of the centroid 1291 within the phase space defining the seizure class 1282), a decrease in seizure severity may be indicated and the patient's condition may be upgraded. However, if L decreases due to seizure class growth (i.e., a size increase in seizure class 1281 as its centroid 1290 moves away from the graph's origin), an increase in seizure severity may be indicated and the patient's condition may be downgraded. It should be noted that for more than two seizure classes, radii r1", r1''', r1$n$' may be determined. Similarly, for non-circular, ellipsoid or non-uniformly shaped seizure classes, different geometrical indications of class size or shape (including major dimensional descriptors, e.g., radius, major axes, etc.) may be applied to describe the size and/or shape of a seizure class.

An increase in the seizure class size for either or both of seizure classes 1281 and 1282 (to classes 1287 and 1288, as shown by arrows L4 and L3), may also indicate that the patient's seizures are becoming more severe (e.g., extreme) and that the patient's condition is deteriorating. That is, the seizure class 1287 may increase in size to a seizure class spread 1296 and/or seizure class 1288 may increase in size to a seizure class spread 1298. Additionally, an increased seizure density in seizure class 1281 and/or seizure class 1282 (e.g., the number of seizures in the class per unit space in the class) may also be indicative of a risk/increased risk of an extreme seizure event/state, that the patient is in an extreme seizure state or that the patient's condition is deteriorating. The appearance or emergence of additional seizure classes (not shown) may be indicative of a risk/increased risk of an extreme seizure event/state, that the patient is in an extreme seizure state, or that the patient's disease state has changed to include additional types of seizures not previously recorded. It is also noted that inter- and intra-class analyses may be used without departing from the spirit and scope of the described embodiments.

In one embodiment, classification analyses may classify seizure events into classes based on groups or clusters of seizures located close to one another in the seizure class phase space. Clustering algorithms may be applied to seizures to classify them based on intensity or inter-seizure interval; two or more of such measure may be combined mathematically into a single index, which may be considered as a seizure severity index. The algorithms may involve a wide variety of mathematical techniques, including, by way of non-limiting examples, average-linkage clustering, canopy clustering algorithms, complete-linkage clustering, DBSCAN (a density based clustering algorithm), expectation-maximization, fuzzy clustering, fuzzy clustering by local approximation of memberships (FLAME), k-means clustering, k-means++, k-medoids, Linde-Buzo-Gray's, Lloyd's, OPTICS, single-linkage clustering and SUBCLU. One or more algorithms may be applied depending on the particular case or needs of the patient.

Seizures may be also classified based on time of occurrence in reference to ultradian or circadian rhythms, such as the sleep-wake cycle, as well as level and type of cognitive or physical activity among others.

Seizure classification may be also uni-variate in the type of metric used (e.g., SSI or ISI) or multi-variate (e.g., multiple SSIs and/or ISIs, SSI and ISI as a function of time of day, time of month, time of year, level or type of activity, etc.). In addition, although FIG. 12 provides an illustration of a two-dimensional phase space, higher-dimensional phase spaces (e.g., 3 or 4-dimensional phase space up to n-dimensional space) may also be used with suitable adaptation in mathematical techniques used.

Seizure classification may be also performed visually (subjectively or objectively) using techniques as described in "The Visual Display of Quantitative Information. E. R. Tufte, 2nd Ed. Graphics Press, Conn. 2007 and "Visual Explanation" E. R. Tufte, Graphics Press. Conn. 2005. FIG. 12 illustrates a method of graphically identifying and displaying seizure classification analyses. Based on the present disclosure, similar methods may be used to mathematically determine seizure classification parameters, which may be displayed or presented to a user in alternative ways.

Figure 13:
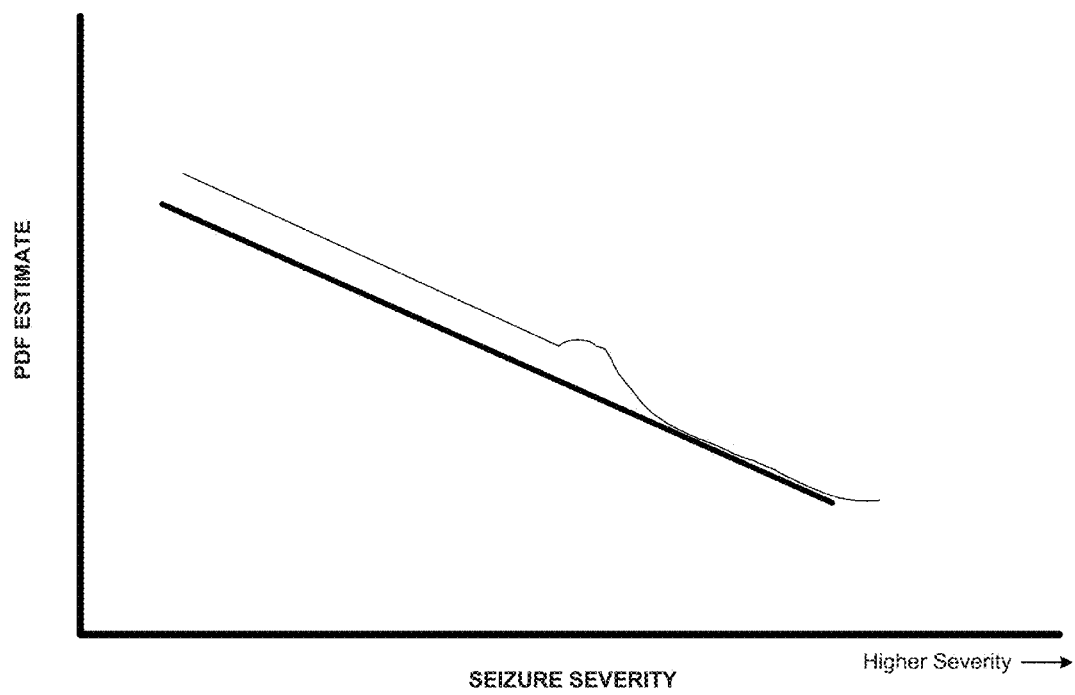
FIG. 13 provides a graphical exemplary representation of the probability density functions of seizure severity, in accordance with one illustrative embodiment of the present invention.

FIG. 13 is a log-log plot of the probability density function (PDF) of seizure energy or severity (x-axis); y-axis corresponds to the PDF estimate of the number of seizures. In particular, FIG. 13 is the exemplary PDF of the severity of seizures from an individual patient over a two year period. The thick curve corresponds to the seizures occurring between Jan. 1, 2010 and Dec. 31, 2010 and the thin curve those between Jan. 1, 2011 and Dec. 31, 2011. Visual inspection of these curves is all that is required to determine that there is a worsening of the patient's epilepsy based on: 1) an increase in the number of more severe seizures on the thin curve (year 2011 seizures) compared to the thick curve (year 2010 seizures); 2) an overall increase in seizure frequency, as represented by the general shift upward of the thin curve compared to the thick curve; and 3) a loss of linearity in the thin curve corresponding to the year 2011, indicating a change in seizure dynamics from a power law distribution (fractal) to a characteristic scale (likely due to an increase or intensification in the coupling level among epileptogenic neuronal ensembles).

Figure 14:
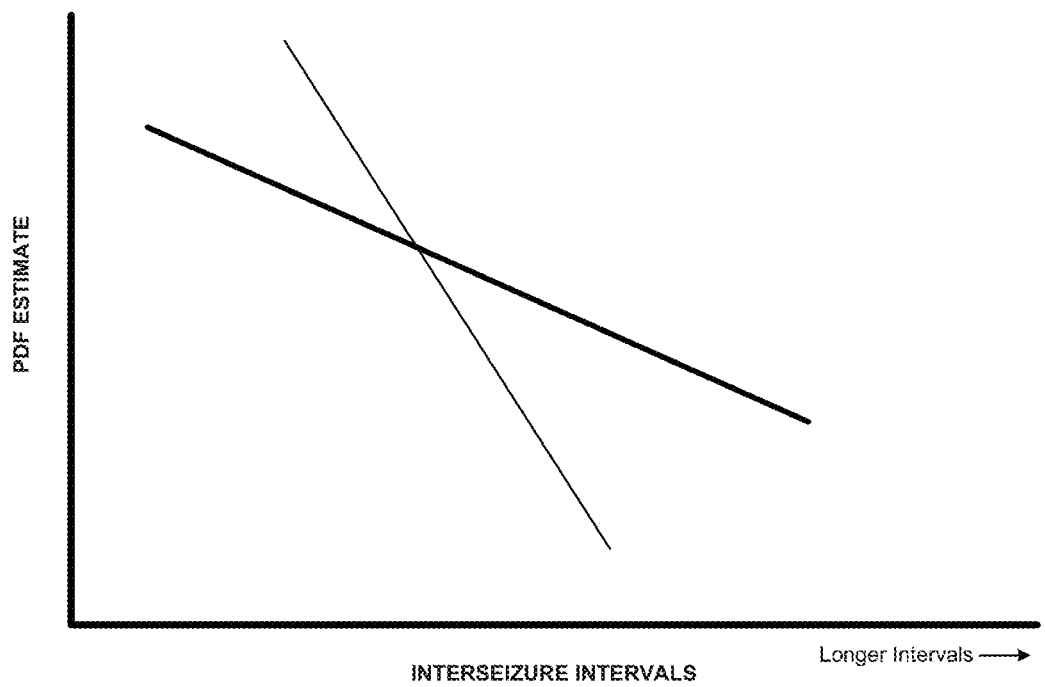
FIG. 14 provides a graphical representation of exemplary probability density functions of inter-seizure intervals, in accordance with one illustrative embodiment of the present invention.

Turning now to FIG. 14, a log-log plot of an exemplary probability density function (PDF) of inter-seizure intervals (e.g., the time elapsed from the onset of a seizure to the onset of the next) in the patient of FIG. 13 is provided. Inter-seizure interval is plotted on the x-axis and the PDF estimate of the number of seizures on the y-axis. The inter-seizure intervals for the patient of FIG. 13 over a two year period are compared to determine if changes in seizure classes have taken place. The thick curve corresponds to the intervals of seizures occurring between Jan. 1, 2010 and Dec. 31, 2010 and the thin curve those between Jan. 1, 2011 and Dec. 31, 2011. Visual inspection of these curves is all that is required to determine that changes in seizure classes have taken place. The number of seizures associated with long inter-seizure intervals in 2011 (thin curve) has decreased compared to the thick curve (year 2010), while the number of seizures having shorter inter-seizure intervals (i.e., seizures occurring relatively close in time to other seizures) have increased. Viewed in the context of the increases in seizure frequency and severity shown for the same patient in FIG. 13, the two Figures illustrate a marked increase in disease burden and thus to overall deterioration in the patient's condition.

Plots of probability density function estimates may be generated using histogram-based estimation methods.

In other embodiments, SSI values may be determined based upon the duration of the seizure event and the peak intensity of the seizure event. In some such embodiments, the SSI may be calculated as the product of the peak intensity of the seizure event and the duration of the seizure event. The peak intensity may be the maximum value of any one, or any number, of body data values during a seizure event. For example, in one illustrative embodiment, a patient's heart rate (HR) may increase above a pre-determined threshold of 85 beats per minute during a seizure event. During the seizure event, the patient's HR may reach a maximum value of 135 beats per minute. For a seizure event lasting 30 seconds, the peak intensity of the seizure event (i.e., 135) may be multiplied by the duration (i.e., 30) to obtain an SSI value. In this example, an SSI above a pre-determined (or adaptable/adaptive) value may indicate an increased risk of extreme event (e.g., status epilepticus). Similarly, an ISI value below a pre-determined (or adaptable/adaptive) percentile based upon historical patient data may indicate a risk of an extreme event. For example, if a given SSI value for a patient is above the ninetieth percentile (or an ISI value is below the tenth percentile) of the patient's past SSI (or ISI) values, the patient may be at an increased risk of having an extreme event.

Indexing seizure events may be used in various embodiments to label and/or classify seizure events and their corresponding severity. For example, in one or more illustrative embodiments, a seizure event ("sz") may be represented, as a function of intensity, duration and seizure spread:

$$sz = f(\text{intensity}, \text{duration}, \text{spread}).$$

If a substitution is made as: x=intensity, y=duration, and z=spread, then:

$$sz = f(x, y, z).$$

An indexed overall seizure metric (OSM) may be determined to be the value sz=f(x, y, z). It should be appreciated that x, y and/or z may be set as zero for various determinations of sz or left out altogether. That is, sz may be a function of:
  (i) one of x, y or z: $OSM_{1x}$, $OSM_{1y}$, $OSM_{1z}$,
  (ii) a function of any two of x, y or z: $OSM_{2xy}$, $OSM_{2xz}$, $OSM_{2yz}$, or
  (iii) a function of all three (intensity and duration and spread): $OSM_{3xyz}$.

In alternate embodiments, an indexed seizure metric (ISM) may be determined as the function of inter-seizure interval, SSI, PI, or TOO. In other embodiments, the indexed seizure metric may be based on two or more of ISI, SSI, PI, or TOO.

In further embodiments, an indexed systemic patient condition (SPC) may be determined as the function of patient impact (PI), either alone or in combination with one or more other factors listed herein. Examples of indexed systemic patient condition described above are not exclusive. It is contemplated that any combination of the above described indexed seizure severities may be used in accordance with the embodiments herein. Similarly, a seizure event "sz" may be a function of any combination of body data (e.g., body data, as described above with respect to FIG. 1). When referring to the possible SPC combinations, the term SPCn may be used.

Similarly, a seizure event time series may be used to label and/or classify multiple seizure events based on their intensity (Si), duration (Sd), extent of spread (Sc) separately or conflated into a seizure severity index (SSI), inter-seizure interval ISI), patient impact (PI), date and time of occurrence (TOO), response to therapy (Tx), level of consciousness (LOC), cognitive (LCA), physical activity (LPA), body position (e.g., upright) (ByP), physical fitness level (PFL) or, quality of life (QOL). Such a time series may be represented as:

Sztime series=f (Si, Sd, Sc, (or SSI), ISI, PI, TOO, Tx, LOC, LCA, LPA, ByP, PFL, QOL), of each seizure included in the time series. An indexed systemic patient condition (iSPC) based on a time series of seizure events (sztime series) may be determined, in some embodiments, as: SPCf (sztime series)

It is noted that the presence or absence of change in classes/clusters/patterns, including disappearance or emergence of classes/clusters/patterns (or parts thereof), is determined to a certain extent by the type of analysis used (e.g., soft vs. hard clustering rules) and by the size/quality (statistically representative or not) of the sample. Therefore, clinical correlation is indicated to better interpret the changes if any in the results of the analyses.

A useful way to address the potential ambiguity of classification results (i.e., whether a particular seizure is or is not within a particular seizure class) is to perform a multivariate classification analysis (e.g., instead of having only one seizure metric based upon ECoG indices, also using one or more additional seizure metrics based, for example, upon kinetic and/or cognitive indices), and to correlate the results with quantitative clinical indices or metrics. For example, if a change in a seizure class is not identified based on seizure severity indices (SSI values) derived from the ECoG, by all (or the majority) of a plurality of seizure class analysis measures, or if there is a non-statistically-significant difference, SSI measured using complex reaction time (a cognitive index) may be used to determine if the lack of agreement or of statistical significance is associated with or has an clinical impact which may be beneficial or deleterious. In this example, a comparison of complex reaction times associated with seizure in the original class and those in the indeterminate classification will be made, with two possible results: if there is no difference in complex reaction time between the original and the unclassified seizures, from a cognitive perspective and clinical impact, the indeterminate class of seizures do not constitute a new class of seizures. On the other hand, if there is a difference in the complex reaction time, the unclassified seizures may be treated as a different or new seizure class.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. A medical device system, comprising:
  a seizure determination unit configured to detect a plurality of seizure events based upon body data of the patient;
  a blood gases acquisition unit configured to acquire oxygen saturation data of a patient;
  a seizure metric determination unit configured to determine, for each seizure event, at least one seizure metric value characterizing the seizure event, wherein each of said at least one seizure metric values is based at least in part on an oxygen saturation index;
  a classification analysis unit configured to perform a first classification of a first portion of the plurality of seizure events, the first classification analysis comprising assigning each seizure event in the first portion to at least one seizure class based upon the proximity of the seizure metric values to each other; and further configured to perform a second classification analysis of a second portion of the plurality of seizure events, the second classification analysis comprising assigning each seizure event in the second portion to at least one seizure class based upon the proximity of the seizure metric values, wherein said second portion comprises at least one seizure event not present in the first portion;
  a classification analysis comparator unit configured to compare the results of the first classification analysis and the second classification analysis;
  and
  a responsive action unit configured to perform at least one of:
   a. reporting a change from the first classification to the second classification;
   b. reporting the absence of a change from the first classification to the second classification;
   c. displaying a result of at least one of the first classification analysis, the second classification analysis, and the comparing;
   d. identifying the emergence of a new class based on the comparing;
   e. identifying the disappearance of a prior class based on the comparing;
   f. identifying one or more outlier seizure events not part of any class;
   g. identifying an effect of a therapy;
   h. providing a therapy to the patient in response to the comparing;
   i. identifying a proposed change in therapy;
   j. identifying a proposed additional therapy;
   k. identifying an extreme seizure event;
   l. identifying a worsening trend in the patient's seizures;
   m. identifying an improvement trend in the patient's seizures;
   n. downgrading the patient's condition in response to a worsening in the patient's seizures; and
   o. upgrading the patient's condition in response to an improvement in the patient's seizures.

2. The medical device system of claim 1, further comprising at least one of a cardiac data acquisition unit configured to acquire cardiac data from the patient, a respiration acquisition unit configured to acquire respiratory data from the patient, or a kinetic unit configured to acquire kinetic data from the patient.

3. The medical device system of claim 2, wherein the seizure determination unit is configured to detect a plurality of seizure events based at least in part upon one or more of cardiac data acquired by the cardiac data acquisition unit, respiratory data acquired by the respiration acquisition unit, or kinetic activity data acquired by the kinetic unit.

4. The medical device system of claim 2, wherein the seizure metric determination unit is configured to determine, for each seizure event, at least one seizure metric value characterizing the seizure event, wherein each of said at least one seizure metric values is further based at least in part on at least one of a cardiac data index, a respiratory index, or a kinetic activity index.

5. The medical device system of claim 4, wherein the seizure metric determination unit is configured to determine at least two seizure metric values;
  wherein the classification analysis unit is configured to identify one or more seizure classes by determining one or more relationships among at least a portion of the plurality of seizure events, wherein the one or more relationships are based on the at least two seizure metric values for each seizure event; and
  wherein the classification analysis comparator unit is configured to identify a change in at least one class of said one or more seizure classes from said first classification analysis to said second classification analysis.

6. The medical device system of claim 1, wherein the classification analysis unit is configured to identify one or more seizure classes by determining one or more relationships among at least a portion of the plurality of seizure events, wherein the one or more relationships are based on the at least one seizure metric value for each seizure event; and wherein the classification analysis comparator unit is configured to identify a change in at least one class of said one or more seizure classes from said first classification analysis to said second classification analysis.

7. The medical device system of claim 1, wherein the responsive action unit is further configured to identify a change in a relationship between a first class and a second class of seizures in moving from the first classification analysis to the second classification analysis.

8. The medical device system of claim 1, wherein the at least one seizure metric value comprises at least one of:
   a seizure severity index,
   an ictal energy level,
   a post-ictal energy level,
   a patient seizure impact, or
   a rate of change of one of the foregoing over at least one of a microscopic, mesoscopic or macroscopic time scale.

9. The medical device system of claim 1, wherein the classification analysis unit is further configured to at least one of:
   identify said classes by at least one mathematical analysis operation selected from a statistical analysis, a graphical analysis, an unsupervised machine learning analysis, a supervised machine learning analysis, and a semisupervised machine learning analysis, wherein the statistical analysis comprises one or more of identifying a measure of central tendency of the class based on the at least one seizure metric,
   determine one or more percentile values based on the at least one seizure metric; and
   determine one or more distributions based on the at least one seizure metric.

10. The medical device system of claim 1, wherein the first seizure class comprises non-extreme seizures and the second class comprises extreme seizures.

11. The medical device system of claim 10, wherein the extreme seizures comprise at least one of seizures having a risk of SUDEP or seizures having an increased risk of SUDEP.

12. The medical device system of claim 1, wherein at least one of the seizure determination unit, the blood gases acquisition unit, the seizure metric determination unit, the classification analysis unit, the classification analysis comparator unit, or the responsive action unit is configured to be implantable in the patient's body.

13. The medical device system of claim 1, wherein at least one of the seizure determination unit, the blood gases acquisition unit, the seizure metric determination unit, the classification analysis unit, the classification analysis comparator unit, or the responsive action unit is configured to be sited externally to the patient's body.

14. The medical device system of claim 1, wherein the blood gases acquisition unit is further configured to only acquire oxygen saturation data of the patient in response to a detection of a seizure event by the seizure determination unit.

15. The medical device system of claim 1, further comprising:
   a cardiac data acquisition unit configured to acquire cardiac data from the patient; and
   a cardiac arrhythmia detection unit configured to identify a cardiac arrhythmia or at least one risk factor for a cardiac arrhythmia from the cardiac data;
   wherein the blood gases acquisition unit is further configured to only acquire oxygen saturation data of the patient in response to an identification of the cardiac arrhythmia or the at least one risk factor for the cardiac arrhythmia.

16. The medical device system of claim 1, wherein the responsive action unit is configured to deliver an oxygen treatment to the patient.

17. The medical device system of claim 1, further comprising:
   a patient seizure impact unit configured to determine a patient impact value of each of the plurality of seizure events on the patient;
   wherein the classification analysis unit is configured to perform a first classification of a first portion of the plurality of seizure events, the first classification analysis comprising assigning each seizure event in the first portion to at least one seizure class based upon the proximity of the patient impact values to each other; and further configured to perform a second classification analysis of a second portion of the plurality of seizure events, the second classification analysis comprising assigning each seizure event in the second portion to at least one seizure class based upon the proximity of the patient impact values, wherein said second portion comprises at least one seizure event not present in the first portion.

18. A medical device, comprising:
   a seizure determination unit configured to detect at least one seizure event based upon body data of a patient;
   a cardiac data acquisition unit configured to receive cardiac data of the patient;
   a kinetic unit configured to acquire kinetic data of the patient;
   a blood gases acquisition unit configured to acquire oxygen saturation data of the patient;
   a seizure metric determination unit configured to determine, for the seizure event, at least one seizure metric value characterizing the seizure event, wherein said at least one seizure metric value is based at least in part on at least one of a cardiac index, a kinetic index, or an oxygen saturation index;
   a classification analysis unit configured to classify the seizure event based at least in part upon the at least one seizure metric value;
   and
   a responsive action unit configured to perform at least one of:
      a. reporting a classification of the seizure event;
      b. identifying the emergence of a new class;
      c. identifying the disappearance of a prior class;
      d. identifying one or more outlier seizure events not part of any class;
      e. identifying an effect of a therapy;
      f. providing a therapy to the patient;
      g. identifying a proposed change in therapy;
      h. identifying a proposed additional therapy;
      i. identifying an extreme seizure event;
      j. identifying a worsening trend in the patient's seizures;
      k. identifying an improvement trend in the patient's seizures;
      l. downgrading the patient's condition in response to a worsening in the patient's seizures; and
      m. upgrading the patient's condition in response to an improvement in the patient's seizures.

19. The medical device of claim 18, wherein the at least one seizure metric value is indicative of at least one of an arrhythmia, an electrocardiogram (EKG) morphology change, or a heart rate variability (HRV) change.

20. The medical device system of claim 18, further comprising:
a patient seizure impact unit configured to determine a patient impact value of the at least one seizure event on the patient;
wherein the classification analysis unit is configured to classify the at least one seizure event, based at least in part upon the patient impact value.

21. The medical device system of claim 18, further comprising:
an event/warning unit configured to issue a warning of at least one of a risk of SUDEP or an increased risk of SUDEP, in response to the at least one action performed by the responsive action unit.

22. A medical device, comprising:
a seizure determination unit configured to detect at least one seizure event based upon body data of a patient;
a cardiac data acquisition unit configured to receive cardiac data of the patient;
a kinetic unit configured to acquire kinetic data of the patient;
a seizure metric determination unit configured to determine, for the seizure event, at least one seizure metric value characterizing the seizure event, wherein said at least one seizure metric value is based at least in part on at least one of a cardiac index or a kinetic index;
a classification analysis unit configured to classify the seizure event based at least in part upon the at least one seizure metric value; and
a responsive action unit configured to perform at least one of:
  a. reporting a classification of the seizure event;
  b. identifying the emergence of a new class;
  c. identifying the disappearance of a prior class;
  d. identifying one or more outlier seizure events not part of any class;
  e. identifying an effect of a therapy;
  f. providing a therapy to the patient;
  g. identifying a proposed change in therapy;
  h. identifying a proposed additional therapy;
  i. identifying an extreme seizure event;
  j. identifying a worsening trend in the patient's seizures;
  k. identifying an improvement trend in the patient's seizures;
  l. downgrading the patient's condition in response to a worsening in the patient's seizures; and
  m. upgrading the patient's condition in response to an improvement in the patient's seizures.

23. The medical device of claim 22, further comprising a blood gases acquisition unit configured to acquire oxygen saturation data of the patient;
wherein the seizure metric determination unit is configured to determine said at least one seizure metric value based at least in part on an oxygen saturation index.

24. The medical device system of claim 22, further comprising:
a patient seizure impact unit configured to determine a patient impact value of the at least one seizure event on the patient;
wherein the classification analysis unit is configured to classify the at least one seizure event, based at least in part upon the patient impact value.

25. The medical device system of claim 22, further comprising:
an event/warning unit configured to issue a warning of at least one of a risk of SUDEP or an increased risk of SUDEP, in response to the at least one action performed by the responsive action unit.

* * * * *